United States Patent
Jozefiak et al.

(10) Patent No.: US 11,911,411 B2
(45) Date of Patent: Feb. 27, 2024

(54) SULFATED GLYCOSAMINOGLYCAN BIOMATERIALS AS PROTEOGLYCAN MIMICS

(71) Applicant: Glycologix, LLC, Beverly, MA (US)

(72) Inventors: Thomas H. Jozefiak, Belmont, MA (US); Richard W. Heidebrecht, Jr., Somerville, MA (US)

(73) Assignee: Glycologix, Inc., Beverly, MA (US)

( * ) Notice: Subject to any disclaimer, the term of this patent is extended or adjusted under 35 U.S.C. 154(b) by 237 days.

(21) Appl. No.: 17/206,643

(22) Filed: Mar. 19, 2021

(65) Prior Publication Data

US 2021/0290657 A1    Sep. 23, 2021

Related U.S. Application Data

(60) Provisional application No. 62/991,804, filed on Mar. 19, 2020.

(51) Int. Cl.

| | |
|---|---|
| *A61K 31/726* | (2006.01) |
| *A61K 47/54* | (2017.01) |
| *A61P 13/10* | (2006.01) |
| *C08B 37/00* | (2006.01) |

(52) U.S. Cl.
CPC .......... *A61K 31/726* (2013.01); *A61K 47/541* (2017.08); *A61K 47/549* (2017.08); *A61P 13/10* (2018.01); *C08B 37/0063* (2013.01)

(58) Field of Classification Search
CPC .... C08B 37/0063–0075; A61K 31/726; A61K 31/727; A61K 31/736; A61K 31/737; A61K 47/36; A61K 47/38; A61K 47/61; A61K 9/0019; A61P 13/10; A61P 117/02; A61P 19/02; A61L 27/20; A61L 27/3658; A61L 27/3679; A61L 27/54
See application file for complete search history.

(56) References Cited

U.S. PATENT DOCUMENTS

| | | |
|---|---|---|
| 8,912,149 B1 | 12/2014 | Rawat et al. |
| 2017/0266223 A1 | 9/2017 | Marcolongo et al. |
| 2019/0136018 A1 | 5/2019 | Marcolongo et al. |
| 2019/0262386 A1 | 8/2019 | Jozefiak |

FOREIGN PATENT DOCUMENTS

| | | |
|---|---|---|
| WO | 2018053276 A1 | 3/2018 |

*Primary Examiner* — Leigh C Maier
(74) *Attorney, Agent, or Firm* — Elmore Patent Law Group, P.C.; Carolyn S. Elmore; Jia Kang

(57) ABSTRACT

Polymer conjugates are provided that are capable of mimicking functions of natural proteoglycans found in the extracellular matrix of connective tissues. The polymer conjugates of the invention have utility in treating a subject suffering soft tissue degenerative conditions. Also provided are simple and scalable chemical processes for the preparation of the polymer conjugates of the invention.

15 Claims, 2 Drawing Sheets

Specification includes a Sequence Listing.

SEQUENCE LISTING

```
<160> NUMBER OF SEQ ID NOS: 20

<210> SEQ ID NO 1
<211> LENGTH: 5
<212> TYPE: PRT
<213> ORGANISM: Artificial Sequence
<220> FEATURE:
<223> OTHER INFORMATION: Sythetic

<400> SEQUENCE: 1

Gly Arg Gly Asp Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Sythetic

<400> SEQUENCE: 2

Pro His Ser Arg Asn
1               5

<210> SEQ ID NO 3
<211> LENGTH: 4
```

```
<212> TYPE: PRT
<213> ORGANISM: Artificial Sequence
<220> FEATURE:
<223> OTHER INFORMATION: Sythetic

<400> SEQUENCE: 3

Arg Glu Asp Val
1

<210> SEQ ID NO 4
<211> LENGTH: 5
<212> TYPE: PRT
<213> ORGANISM: Artificial Sequence
<220> FEATURE:
<223> OTHER INFORMATION: Sythetic

<400> SEQUENCE: 4

Tyr Ile Gly Ser Arg
1               5

<210> SEQ ID NO 5
<211> LENGTH: 6
<212> TYPE: PRT
<213> ORGANISM: Artificial Sequence
<220> FEATURE:
<223> OTHER INFORMATION: Sythetic

<400> SEQUENCE: 5

Gly Ile Ile Phe Phe Leu
1               5

<210> SEQ ID NO 6
<211> LENGTH: 5
<212> TYPE: PRT
<213> ORGANISM: Artificial Sequence
<220> FEATURE:
<223> OTHER INFORMATION: Sythetic

<400> SEQUENCE: 6

Ile Lys Val Ala Val
1               5

<210> SEQ ID NO 7
<211> LENGTH: 13
<212> TYPE: PRT
<213> ORGANISM: Artificial Sequence
<220> FEATURE:
<223> OTHER INFORMATION: Sythetic

<400> SEQUENCE: 7

Ser Tyr Ile Arg Ile Ala Asp Thr Asn Ile Thr Gly Cys
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Sythetic

<400> SEQUENCE: 8

Leu Arg Glu Leu His Leu Asn Asn Asn
1               5

<210> SEQ ID NO 9
<211> LENGTH: 9
<212> TYPE: PRT
```

```
<213> ORGANISM: Artificial Sequence
<220> FEATURE:
<223> OTHER INFORMATION: Sythetic

<400> SEQUENCE: 9

Leu His Glu Arg His Leu Asn Asn Asn
1               5

<210> SEQ ID NO 10
<211> LENGTH: 19
<212> TYPE: PRT
<213> ORGANISM: Artificial Sequence
<220> FEATURE:
<223> OTHER INFORMATION: Sythetic

<400> SEQUENCE: 10

Gly Leu Arg Ser Lys Ser Lys Lys Phe Arg Arg Pro Asp Ile Gln Tyr
1               5                   10                  15

Pro Asp Ala

<210> SEQ ID NO 11
<211> LENGTH: 20
<212> TYPE: PRT
<213> ORGANISM: Artificial Sequence
<220> FEATURE:
<223> OTHER INFORMATION: Sythetic

<400> SEQUENCE: 11

Arg Arg Ala Asn Ala Ala Leu Lys Ala Gly Glu Leu Tyr Lys Ser Ile
1               5                   10                  15

Leu Tyr Gly Cys
            20

<210> SEQ ID NO 12
<211> LENGTH: 8
<212> TYPE: PRT
<213> ORGANISM: Artificial Sequence
<220> FEATURE:
<223> OTHER INFORMATION: Sythetic

<400> SEQUENCE: 12

Trp Tyr Arg Gly Arg Leu Gly Cys
1               5

<210> SEQ ID NO 13
<211> LENGTH: 10
<212> TYPE: PRT
<213> ORGANISM: Artificial Sequence
<220> FEATURE:
<223> OTHER INFORMATION: Sythetic

<400> SEQUENCE: 13

Lys Glu Leu Asn Leu Val Tyr Thr Gly Cys
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Sythetic

<400> SEQUENCE: 14

Gly Ser Ile Thr Thr Ile Asp Val Pro Trp Asn Val Gly Cys
1               5                   10
```

```
<210> SEQ ID NO 15
<211> LENGTH: 15
<212> TYPE: PRT
<213> ORGANISM: Artificial Sequence
<220> FEATURE:
<223> OTHER INFORMATION: Sythetic

<400> SEQUENCE: 15

Trp His Cys Tyr Thr Tyr Phe Pro His His Tyr Cys Val Tyr Gly
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Sythetic

<400> SEQUENCE: 16

Gly Trp His Cys Tyr Thr Tyr Phe Pro His His Tyr Cys Thr Tyr Gly
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Sythetic

<400> SEQUENCE: 17

Ala Trp His Cys Tyr Thr Tyr Phe Pro His His Tyr Cys Val Tyr Gly
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Sythetic

<400> SEQUENCE: 18

Leu Trp His Cys Tyr Thr Tyr Phe Pro His His Tyr Cys Val Tyr Gly
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Synthetic

<400> SEQUENCE: 19

Tyr Trp His Cys Tyr Thr Tyr Phe Pro His His Tyr Cys Val Tyr Gly
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Sythetic

<400> SEQUENCE: 20

Gly Ala His Trp Gln Phe Asn Ala Leu Thr Val Arg Gly Gly Gly Cys
1               5                   10                  15
```

SULFATED GLYCOSAMINOGLYCAN BIOMATERIALS AS PROTEOGLYCAN MIMICS

RELATED APPLICATION

This application claims the benefit of U.S. Provisional Application No. 62/991,804, filed on Mar. 19, 2020. The entire contents of the above-identified application are herein incorporated by reference.

SEQUENCE LISTING

The sequence listing submitted via EFS, in compliance with 37 CFR § 1.52(e)(5), is incorporated herein by reference. The sequence listing file submitted via EFS contains the file "4252.3002 US1 Seq List_ST25", created on Sep. 14, 2023, which is 4,392 bytes in size.

BACKGROUND

The extracellular matrix (ECM) forms the non-cellular scaffolding of soft and connective tissues. It provides both the biochemical and structural support needed by resident cells and it plays a critical role in maintaining tissue shape and resisting mechanical stress. Proteoglycans are native macromolecules of the ECM that maintain tissue health and prevent ECM degradation. Through their strong osmotic hydration and ability to bind and modulate key growth factors, proteoglycans are the protectors of a healthy ECM. As a response to aging, disease, or damage, the ECM loses functionality. Proteoglycan content diminishes and causing collagen fibers and other matrix components to also begin to degrade. Such degradation is an underlying factor in a number of soft tissue diseases, disorders, and/or conditions, including those of the skin, spinal disc, cartilage, and urethral tissue to name but a few. The restoration of proteoglycan functionality is one treatment option for addressing the loss of ECM functionality.

WO2018/053276, which is incorporated herein by reference in its entirety, by Thomas Jozefiak, designating the US and published on Mar. 22, 2018, describes novel proteoglycan mimic biopolymers. Preferred materials are derived from a process including the activation of a core polymer with a bifunctional linking agent followed by the addition of an excess of a sulfated glycosaminoglycan (GAG) to react with the activated core polymer. A process is also described in which additional modifiers are included to impart additional desirable properties, such as targeting to specific biological targets. It has now been discovered that improved proteoglycan mimic compositions can be more effectively produced by a process allowing better control over the addition of modifiers in a subsequent step.

SUMMARY OF THE INVENTION

The present disclosure describes polymer conjugates of moderate to high molecular weight that are soluble in aqueous and biological solutions and are comprised of sulfated glycosaminoglycan (GAG) chains and modifiers. Provided polymer conjugates are biocompatible, easy to inject using small gauge needles, are capable of mimicking certain proteoglycan functions in soft tissue ECM and have improved targeting and/or local reactivity. The present disclosure also provides methods of treating subjects suffering from soft tissue degenerative conditions.

The invention is based, in part, upon the unexpected discovery that the prior art process often results in the retention of pendant reactive groups derived from incomplete reaction of the linker reagent. This observation was unexpected in view of the reactivity of the pendant linker groups and the availability of polymer bound hydroxyl groups which are reactive in the high-pH environment of the reaction as well as hydroxide ion itself. The inventors have found that the presence of these pendant reactive groups can be controlled by selection of reaction conditions. The current inventive process is based on the recognition that this reactive compound has utility as an intermediate in the preparation of modified compositions. The novel inventive process selects conditions that produce a controllable level of pendant reactive groups in the intermediate biopolymer, and then introduces a reactive modifier group in excess to fully quench remaining reactive linker groups. The resulting 3-stage process has strong advantages over the prior art process in which the modifier group was introduced simultaneously with the GAG biopolymer. Under those conditions, the desired buildup of high molecular weight was severely restrained due to scavenging of vinylsulfone groups by the more highly reactive quencher.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF CERTAIN EMBODIMENTS

Figure 1:
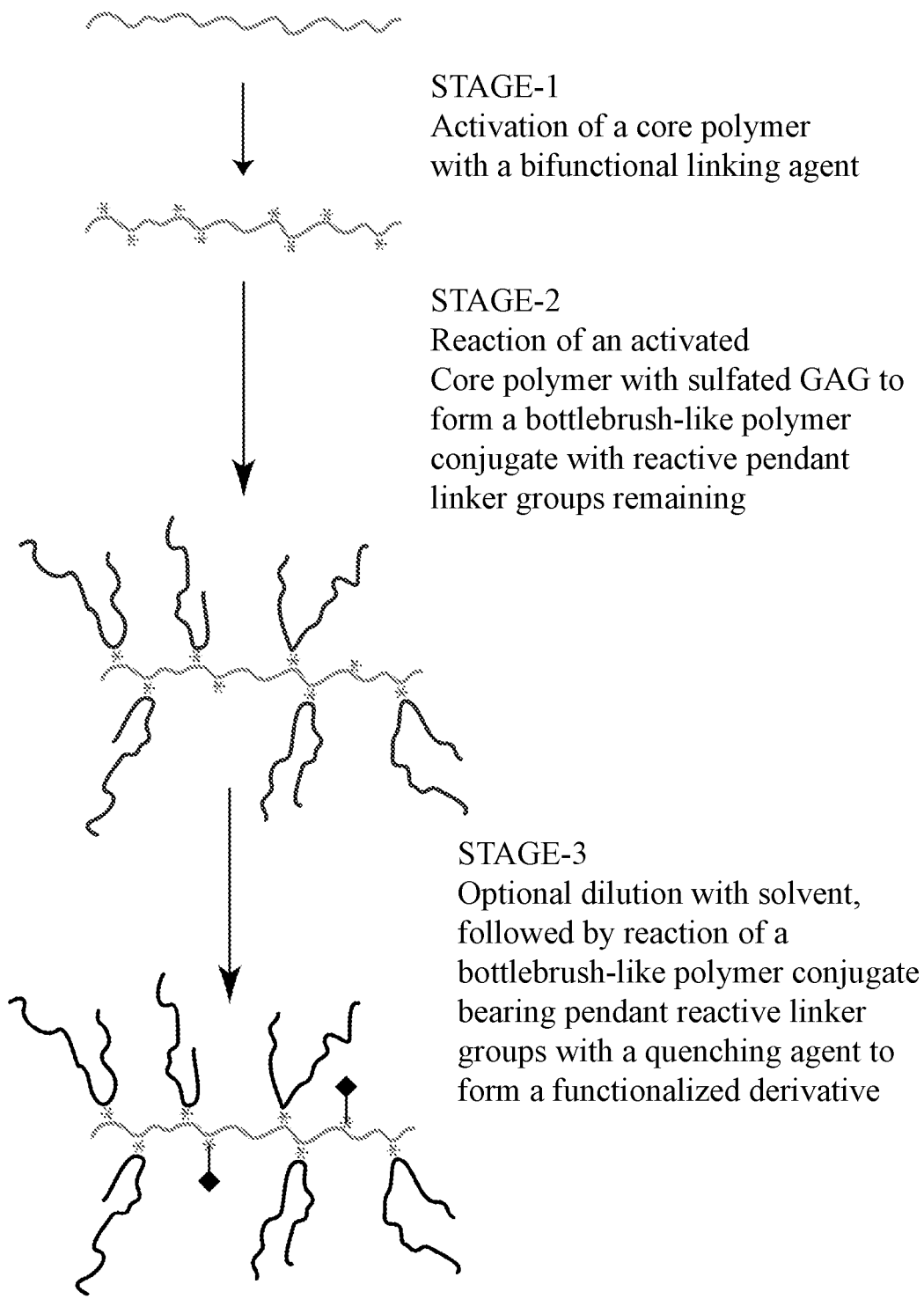
FIG. 1 depicts activation of a linear polymer with a bifunctional linking agent followed by linking of the activated polymer with sulfated GAG chains to form a bottle-brush-like polymer conjugate characterized by reactive pendant linker groups remaining. An optional dilution is followed by reaction of the pendant linker groups with a modifier or quenching agent.
Figure 2:
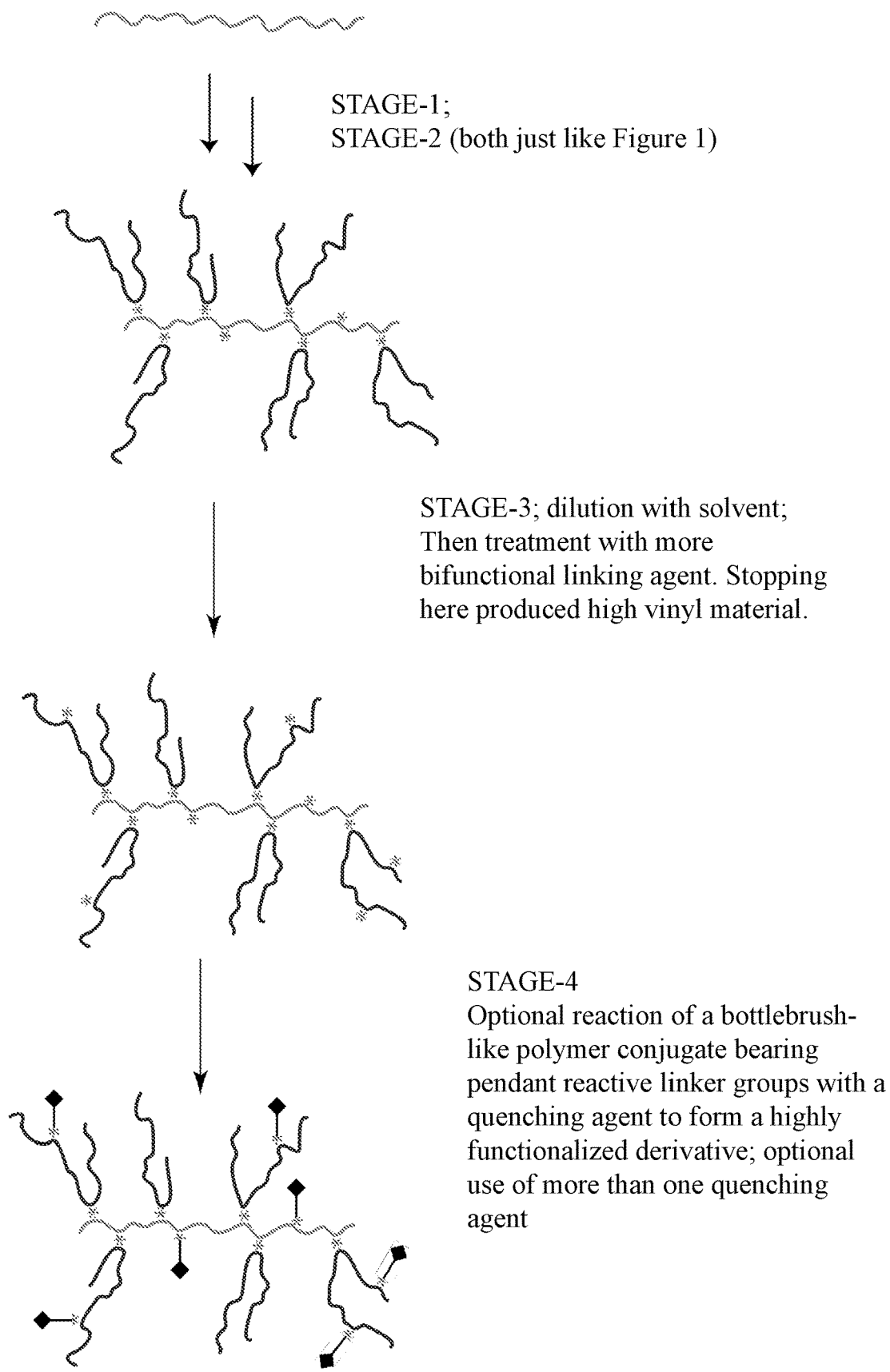
FIG. 2 depicts activation of a linear polymer with the bifunctional linking agent followed by linking of the activated polymer with sulfated GAG chains to form a bottle-brush-like polymer conjugate characterized by reactive pendant linker groups remaining; the optional dilution, the addition of the same or different bifunctional agent (such as divinyl sulfone), the optional addition of a modifier or quenching agent and the optional addition of more than one quenching agent.

In order to address a long-felt need in the treatment of soft tissues diseases, disorders, and conditions, it is desirable to produce proteoglycan mimics that are capable of mimicking the morphology and physical properties of natural proteoglycans. Natural proteoglycans are comprised of GAG chains that are highly negatively charged under physiological conditions due to the presence of sulfate and carboxylate groups.

The present invention relates to reacting sulfated GAGs and other reactive moieties in a controlled way to produce high molecular weight, branched, sulfated GAG compositions that remain soluble in aqueous solutions.

Definitions

As used herein, headers and section subtitles are provided for organizational purposes and are not meant to be limiting. Therefore, embodiments described in one section apply to the entirety of the application, unless otherwise specified.

The term "approximately" or "about", as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The term "administration", as used herein, typically refers to the administration of a composition to a subject or system. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravesical, intravenous, intraventricular, within a specific organ (e.g., intrahepatic), mucosal, nasal, oral, rectal, subcutaneous, sublingual, topical, tracheal (e.g., by intratracheal instillation), vaginal, vitreal, etc. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time. As used herein, "biocompatible" is intended to describe materials that exert minimal destructive or host response effects while in contact with body fluids or living cells or tissues. The term is also taken to mean that which results in minimal interactions with recognition proteins, e.g., naturally occurring antibodies, cell proteins, cells and other components of biological systems, unless such interactions are specifically desirable. Thus, materials and functional groups specifically intended to cause the above effects and whose administration in vivo induces minimal and medically acceptable inflammation, foreign body reaction, immunotoxicity, chemical toxicity or other such adverse effects are considered to be biocompatible. The term "biomolecule", as used herein, refers to molecules (e.g., proteins, amino acids, peptides, polynucleotides, nucleotides, carbohydrates, sugars, lipids, nucleoproteins, glycoproteins, lipoproteins, steroids, etc.) which belong to classes of chemical compounds, whether naturally occurring or artificially created (e.g., by synthetic or recombinant methods), that are commonly found in cells and tissues. Exemplary types of biomolecules include, but are not limited to, peptides, enzymes, receptors, neurotransmitters, hormones, cytokines, cell response modifiers such as growth factors and chemotactic factors, antibodies, vaccines, interferons, ribozymes, anti-sense agents, plasmids, DNA, and RNA.

The term "treatment" (also "treat" or "treating"), as used herein, refers to any administration of a substance (e.g., pharmaceutical composition) that partially or completely alleviates, ameliorates, relives, inhibits, delays onset of, reduces severity of, and/or reduces incidence of one or more symptoms, features, and/or causes of a particular disease, disorder, and/or condition. Such treatment may be of a subject who does not exhibit signs of the relevant disease, disorder, and/or condition and/or of a subject who exhibits only early signs of the disease, disorder, and/or condition. Alternatively or additionally, such treatment may be of a subject who exhibits one or more established signs of the relevant disease, disorder, and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

As used herein "subject" means an organism, typically a mammal (e.g., a human). In some embodiments, a subject is suffering from a relevant disease, disorder, or condition. In some embodiments, a subject is susceptible to a disease, disorder, or condition. In some embodiments, a subject displays one or more symptoms or characteristics of a disease, disorder, or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered. In some embodiments, for any of the methods described herein, a subject is a mammal. In some embodiments, for any of the methods described herein, a subject is a human.

The terms "glycosaminoglycan" and "GAG", as used interchangeably herein, refer to a polysaccharide comprised of a repeating disaccharide unit comprising an amino sugar (such as N-acetylglucosamine or N-acetylgalactosamine), and a uronic sugar (such as glucuronic acid or iduronic acid), or galactose. The GAGs for use in the present invention may vary in size and be either sulfated or non-sulfated. The GAGs which may be used in the methods of the invention include, but are not limited to, hyaluronic acid, chondroitin, chondroitin sulfates (e.g., chondroitin 6-sulfate and chondroitin 4-sulfate), heparan, heparan sulfate, heparin, dermatan, dermatan sulfate, keratan sulfate, and the like.

The terms "improve," "increase" or "reduce," as used herein or grammatical equivalents thereof, indicate values that are relative to a baseline measurement, such as a measurement in the same individual prior to initiation of a treatment described herein, or a measurement in a control individual (or multiple control individuals) in the absence of the treatment described herein.

As used herein, the term "modifier" refers to an organic, inorganic or bioorganic moiety that is covalently attached to a polymer conjugate. Modifiers can be small molecules or macromolecules, and can belong to any chemical or pharmaceutical class, e.g., nucleotides, chemotherapeutic agents, antibacterial agents, antiviral agents, immunomodulators, hormones or analogs thereof, enzymes, inhibitors, alkaloids and therapeutic radionuclides a therapeutic radionuclide (e.g., alpha, beta or positron emitter). In certain embodiments, modifier according to the invention include, but are not limited to, biomolecules, small molecules, therapeutic agents, pharmaceutically useful groups or entities, macromolecules, diagnostic labels, chelating agents, hydrophilic moieties, dispersants, charge modifying agents, viscosity modifying agents, surfactants, coagulation agents and flocculants, to name a few. In some embodiments, a modifier is a target peptide or carbohydrate having affinity for a particular biomolecule or tissue and may enhance delivery and/or efficacy of a polymer conjugate. A modifier can have one or more pharmaceutical functions, e.g., biological activity and pharmacokinetics modification. Pharmacokinetics modifiers can include, for example, antibodies, antigens, receptor ligands, hydrophilic, hydrophobic or charged groups. Biologically active modifiers include, for example, therapeutic drugs and prodrugs, antigens, immunomodulators. Detectable modifiers include diagnostic labels, such as radioactive, fluorescent, paramagnetic, superparamagnetic, ferromagnetic, X-ray modulating, X-ray-opaque, ultrasound-reflective, and other substances detectable by one of available clinical or laboratory methods, e.g., scintigraphy, NMR spectroscopy, MRI, X-ray tomography, sonotomography, photoimaging, radioimmunoassay.

Preferred modifiers are characterized by a reactive moiety capable of reacting with a pendant reactive group resulting from the reaction of a bifunctional linker and polymer core. For example, the reaction of divinyl sulfone (DVS) and chondroitin sulfate results in a polymer core characterized by pendant vinyl groups. Nucleophilic groups, preferably amines and/or sulfhydryl groups, are reactive with such pendant vinyl groups. Accordingly, where the pendant reactive group is a vinyl group, a preferred modifier is characterized by an amine.

The term "hydrophobic" refers to a property of an organic molecule or radical that is not or is not expected to have significant solubility in water or aqueous solutions. A hydrophobic moiety is taken to denote a substituent group on an organic molecule or polymer that diminishes the aqueous solubility of the parent molecule or polymer. The hydrophobic moiety may comprise a C4-C36 alkyl group, such as a fatty acid, or sterol which may be saturated or un-saturated. In some embodiments, C10, C12, C14, C16, C18, C20, C22, C24, C26, C28, C30, C32 and C34 fatty acids may be used. The hydrophobic group may have 16 or more carbon atoms. Exemplary suitable hydrophobic groups may be selected from the group comprising: sterol, cholesterol, palmitoyl, hexadec-8-enoyl, oleyl, (9E,12E)-octadeca-9,12-dienoyl, dioctanoyl, sphingoid, and C16-C20 acyl. For example, the hydrophobic modifier can be, or may comprise a lipid, a phospholipid or a lipophilic alcohol, such as a cationic lipids, a neutral lipids, sphingolipids, and fatty acids such as stearic, oleic, elaidic, linoleic, linoleaidic, linolenic, and myristic acids. In some embodiments the fatty acid comprises a C4-C30 saturated or unsaturated alkyl chain. The alkyl chain may be linear or branched.

The terms "linker", "linking agent", "crosslinking agent" and the like include agents that possess one or more reactive functionalities that can react with two or more molecules, thereby "linking" them. The linking agent can link, for example, a polymer to a GAG, two GAGs, and a GAG and a modifier. Linking agents are generally known in the art. A particularly preferred linker is divinylsulfone.

The term "prevent" or "prevention", as used herein when used in connection with the occurrence of a disease, disorder, and/or condition, refers to reducing the risk of developing the disease, disorder, and/or condition and/or to delaying onset of one or more characteristics or symptoms of the disease, disorder, or condition. Prevention may be considered complete when onset of a disease, disorder, or condition has been delayed for a predefined period of time.

The term "reference", as used herein, describes a standard or control relative to which a comparison is performed. For example, in some embodiments, an agent, animal, individual, population, sample, sequence, or value of interest is compared with a reference or control agent, animal, individual, population, sample, sequence, or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control. In some embodiments, a reference is aggrecan. In some embodiments, a reference is a polymeric starting material. In some embodiments, a reference is a null conjugation reaction. In some embodiments, the reference is a null conjugation reaction identical in all respects to formation of a provided polymer conjugate except for the omission of a linker agent.

The term, "gel", refers to viscoelastic materials whose rheological properties distinguish them from solutions or solids. A composition is considered to be a gel if it does not flow under steady state or low shear conditions but show some fluidity or flow when agitated. Gels consist of 3-dimensional extended networks that constitute a continuous solid phase into which a fluid phase is dispersed (water, in the case of a hydrogel). In general, the fluid phase is present in far greater quantity over the solid phase. The extended crosslinked network can be formed through either chemical covalent bonds, or physical associations in solution.

The term "molecular weight", unless otherwise specified, refers to weight average molecular weight or "Mw" (used interchangeably herein with "Mw").

The term "soluble", refers to the chemical condition of a molecule (solute) being completely dispersed at a molecular level in another substance (solvent) wherein there are no strong interactions between solute molecules.

Proteoglycans

Proteoglycans are glycoproteins found in the extracellular matrix (ECM) of all connective tissues of the body. A large number of proteoglycans and their tissue-specific expression have been identified. Although there is considerable diversity of structure, the common structural element of all proteoglycans is a protein core glycosylated with one or many sulfated glycosaminoglycan (GAG) chains. The protein core can contain several modular structural elements important for biological functions (e.g., IgG-like, EGF-like, HA-binding motif, leucine-rich motifs, etc.). The covalently bound sulfated GAG chains are most typically chondroitin sulfate, dermatan sulfate, keratan sulfate, or heparan sulfate. These are often attached to the protein core as O-linked glycans bound to a serine moiety on the core protein chain.

Hydration is critically important for ECM homeostasis. Water content determines tissue volume and resistance to compression. Hydration also creates space required for cellular migration, organization of ECM structural components such as collagen and elastin, and the transport of biomolecules. A major structural function of proteoglycans in the ECM is maintenance of hydration. This is particularly relevant for the large aggregating proteoglycans bearing a large number of sulfated GAG chains. Proteoglycans in the hyalectan family, such as aggrecan and versican contain multiple (e.g., about 10-100) GAG chains concentrated within specific subunits of the core protein. These unique biopolymer structures have a bottlebrush-like polymer architecture and a very high density of anionic charge derived from the large number of sulfate and carboxylate moieties on the GAG chains concentrated in a small volume. In addition to providing critical hydration and structural support in the ECM, proteoglycans are known to play a significant role in extracellular signaling. They are known to bind strongly with several growth factors, chemokines, and cytokines and influence signaling pathways for apoptosis, cellular development, cell motility and adhesion.

A growing body of scientific evidence supports a significant role for proteoglycans in maintaining connective tissue integrity: protecting against tissue degradation, promoting healing after injury, and resisting disease. Because of the important role proteoglycans play in determining the physical properties of connective tissues, and the understanding that age-related changes in connective tissues such as the dermis correlate with proteoglycan degradation, proteoglycan-based therapeutics such as proteoglycan-replacement therapy are a promising approach for treating age-related changes and wound healing, and in addressing unmet medical needs in dermatology, urology, cardiovascular, and orthopedic areas.

Although proteoglycans are understood to be critically important biomolecules in the ECM of cartilage and soft tissues, they are present only in small quantity in most tissues. Proteoglycans are difficult to isolate from natural sources and purify at large scale. Hence, biomolecules such as aggrecan are currently available only as research tools in small quantity. Use of tissue-isolated proteoglycans as therapeutics is cost prohibitive and impractical. Moreover, proteoglycans extracted from xenobiotic tissues (bovine, porcine, marine) may be inappropriate for direct use in human medicine due to immunological host response.

Proteoglycan Mimic Materials

There have been several studies seeking to design compositions capable of mimicking the important structural and/or biological functions of naturally occurring proteoglycans (PG) in connective tissues. These approaches fall into a number of categories:

a. Sulfation of synthetic polymers or natural polysaccharides. For example, one of the simplest approaches for the synthesis of PG mimics is the sulfation of carbohydrates such as dextran [D Papy-Garcia, et. al., Macromolecules 2005, 38:4647-4654]. The sulfation of synthetic polymers such as aromatic polyphenols have also been reported to produce molecules with bioactivity of GAGs or PGs [UR Desai, Future Med. Chem. 2013, 5:1363-1366].

b. Attachment of sulfated GAGs to surfaces or particles. For example, chondroitin sulfate was conjugated to the surface of carbon nanotube to provide GAG-functional nanoparticles as PG mimics in a hydrogel construct for cartilage replacement [J Wei, et. al., Materials Chemistry and Physics 2015, 166:66-72]. Chondroitin sulfate was attached to surfaces of agarose gels after activation of those gels with a reactive cyanate ester capable of reacting with a serine moiety on the chondroitin sulfate reducing end [K J Mattern, et. al., Carbohydrate Research 2007, 342:2192-2201]. Chondroitin sulfate was attached to poly(ethylene terephthalate) fiber surfaces and chitosan-coated PET fiber surfaces [C-H Jou, et. al., Polym. Adv. Technol. 2005, 16:821-826].

c. Creation of insoluble particles by complexation of anionic sulfated GAGs with cationic polymers. The formation of a complex between highly anionic GAGs and polycations such as chitosan has been described as a method to generate nanoparticles capable of binding FGF-2 [S Boddohi, et. al., Biomacromolecules 2009, 10:1402-1409] [LW Place et al., Biomacromolecules 2014, 15:3772-3780]. Heparan was complexed with various reactive polymers to from an insoluble coating applied to medical device surfaces [US2005/0281857].

d. Conjugation of certain bioactive peptides with sulfated GAGs to provide well-defined, soluble peptidoglycan derivatives. For example, the conjugation of dermatan sulfate with peptides capable of binding either collagen-II or hyaluronic acid have been extensively explored and described [S Sharma, et. al., Acta Biomaterialia 2013, 9:4618-4625] [J C Bernhard, et. al., Acta Biomaterialia 2012, 8:1543-1550] [U.S. Pat. No. 9,200,039].

e. Polymerization of monomers bearing a sulfated disaccharide or oligosaccharide. For example, polymer mimics of chondroitin sulfate have been made via synthesis of ROMP polymerizable monomers substituted with a simple chondroitin sulfate disaccharide unit [S-G Lee, et, al., Chem. Sci., 2010, 1:322-325].

f. Synthesis of multivalent oligosaccharide glycans. Specific di- and tetra-saccharides representing single entity heparan sulfate (HS) structural motifs have been prepared and bound to a 4-arm dendritic linking molecule. These heparan sulfate mimics were found to have the ability to mimic the performance of long chain natural HS in their interactions with certain therapeutic proteins [P C Tyler, et. al., Angew. Chem. Int. Ed. 2015, 54: 2718-2723].

g. Conjugation of GAGs with other polymers. For example, several small sugars and oligo saccharides have been conjugated to synthetic polymers by the reaction of their reducing ends with complementary functionality on the synthetic polymer core [K Godula, et. al., J. Am. Chem. Soc. 2010, 132: 9963-9965]. In a related approach, aggrecan-like bottlebrush compositions have been reported using a hyaluronic acid derivative as a polymeric core capable of reacting with the reducing end of full length natural heparan or chondroitin sulfate chains as bristles [L W Place, et al., Biomacromolecules 2014, 15:3772-3780]. In another approach for forming a bottlebrush structure, chondroitin sulfate bearing an O-linked serine glycan at the reducing end of the chain has been used as a monotelechelic amine in several reaction scenarios including an amide forming reaction with poly(acrylic acid) as a core [US20130052155 A1].

A distinct area of research with some relevance to the field of proteoglycan mimics focuses on crosslinked GAG hydrogels. In these cases, extended crosslinked networks are obtained rather than soluble polymeric compounds. The properties of crosslinked networks are most fundamentally derived from their crosslink density and particle size. In contrast, soluble polymers are characterized by their molecular weight and degree of branching. In general, crosslinked gels have high modulus and can be difficult to administer by injection.

A water swollen hydrogel particle prepared through the crosslinking of a GAG material presents a GAG-rich surface in a biological environment. However, after injection into tissue these crosslinked gels behave as discrete particles within the ECM, and therefore cannot function as proteoglycan mimic materials. They do not have the ability to integrate into soft tissue and interact with other components of the ECM in the way a proteoglycan such as versican, for example, is known to do in the dermis.

Research on crosslinked GAG networks can focus on hyaluronic acid (HA), owing to its large scale production from bacterial culture as well as natural sources and commercial availability. Furthermore, HA is generally available in very high molecular weight form, usually above 500,000 Da and extending to several million Da. High molecular weight favors the formation of extended hydrogel structures. For this reason, there has been significant work on the synthesis and use of HA-based crosslinked hydrogels, and hyaluronic acid is a widely used GAG in biopharma and medical device product development. HA gels are well known as dermal fillers, viscosupplements, and cosmetics.

In contrast to HA, sulfated GAGs (e.g., chondroitin sulfate, dermatan sulfate, heparan sulfate, and keratan sulfate), are currently available from natural sources, and generally in much smaller quantity. Commercial sources of high quality GMP material are limited. Also, as extracted from natural tissues, these sulfated GAGs are found to have much lower molecular weight than HA. For example, high quality bovine sourced chondroitin sulfate is generally found with molecular weight below 50,000 Da, and typically below 25,000 Da. The low molecular weight of these biopolymers as well as the difficulty of sourcing high purity material has limited their use in biopharma and medical device product development.

Research reports and patents on crosslinked HA hydrogels have noted that other GAGs may be utilized in the place of HA. However, given the significant dissimilarities between sulfated GAGs and HA, most notably the very large difference in molecular weight, existing synthetic methods for forming gels with HA cannot be assumed to be applicable to sulfated GAGs. Also, the properties of crosslinked hydrogels from sulfated GAGs cannot be assumed to resemble those of HA crosslinked hydrogels.

For the formation of crosslinked GAG hydrogels, several 1-step direct linking agents have been described in the literature and have been found to provide biocompatible hydrogels. These crosslinked HA hydrogels have been utilized in a variety of commercial products such as dermal fillers (e.g., HYLAFORM®, PREVELLE®, RESTYLANE®, JUVEDERM®) and viscosupplements (e.g., SYNVISC®, SYNVISC-ONE®, SUPARTZ®, EUFLEXXA®, JONEXA®, MONOVISC®, ORTHOVISC®) and adhesion barriers (e.g., INCERT®, INCERT-S®, HYALOBARRIER®). Non-limiting examples of direct linking agents are divinylsulfone (DVS), epichlorohydrin (epi), butanediol diglycidylether (BDDE), diepoxy octane, ethyleneglycol diglycidyl ether, phenylene-bis(ethyl carbodiimide), 1,1'carbonyldiimidazole (CDI).

The reaction of various direct crosslinkers with a sulfated GAG is known to form a strong hydrogel. However, Applicants have observed that such gel formation is sensitive to reaction conditions and unexpected results can be obtained. For example, the reaction of DVS with chondroitin sulfate may result in several outcomes. In some cases, a strong and clear gel is obtained. In some cases, a viscous clear fluid is obtained. In some cases, a cloudy suspension of an insoluble modified chondroitin sulfate is obtained. In some cases, a cloudy gel is obtained. Applicant discloses herein methods for controlling and directing these various outcomes to produce soluble polymer conjugates. Of course, the word "soluble" in this context refers to water-soluble in which the solution is freely flowing and injectable.

Despite the several attempts at developing proteoglycan mimic materials, there is currently no known polymer conjugate that effectively provides the beneficial physical and biological function of natural proteoglycans, is known or is expected to be biocompatible, is soluble and able to integrate into soft tissue by diffusion, is easy to inject or administer, is retained in soft tissue for an extended period of time, and can be made using an efficient and simple chemical process scalable to commercial quantities.

Polymer Conjugates

The present invention relates to proteoglycan mimics. The present invention encompasses the recognition that sulfated GAGs (and other polymers) contain a number of functional moieties that are capable of reaction with an appropriate linking agent to form soluble, higher order polymer conjugates, including those having branched and bottlebrush-like architectures. Such functional moieties may be reacted with a linking agent to "activate" a polymer chain for conjugation with one or more other polymer chains. While prior efforts on this front have generated GAG compositions that are gels, the present invention provides polymer conjugates that are not gels and remain soluble in aqueous solution. In some embodiments, soluble polymer conjugates of the present invention are produced by controlling the stoichiometry of the linking agent and sulfated GAG, the concentration of sulfated GAG, the molecular weight of the sulfated GAG, and/or and reaction time.

Again, the word "soluble" in this context refers to water-soluble in which the solution is freely flowing and injectable. "Freely flowing" preferably means a viscosity of less than about 500 cp at 20 C, preferably less than about 100 cp, such as less than about 50 cp. "Injectable" typically refers to the delivery through a medical needle used for intravenous, intramuscular or subcutaneous injection. For example, 15-30 gauge needles, preferably 18-25 gauge needles can be used. With higher gauge needles and/or viscosity, more time and pressure may be required to deliver a particular solution. Where the viscosity is too great in combination with a needle that is too small, injection failures are likely. An injection failure is where the needle clogs during delivery. Thus, the water-solubility of a proteoglycan mimic can be characterized, at least in one aspect, by the viscosity of an aqueous solution. Such an aqueous solution can be measured at the point of saturation. It will be appreciated, however, that the solution that is administered need not be delivered at saturation. Alternatively or additionally, the solution can be microfilterable. For example, the solution can be passed through a filter (e.g., a 0.2 micron filter), thereby rendering the solution sterile and, preferably, suitable for injection.

Functional moieties on a GAG or other polymers that may be utilized in linking chemistries described herein include, without limitation, hydroxyl groups, amines, thiols, and carboxyl groups. In some embodiments, a functional moiety is or comprises one or more hydroxyl groups along a GAG polymer backbone chain. In some embodiments, a functional moiety is or comprises one or more carboxyl groups along a GAG polymer backbone chain.

In some embodiments, polymer conjugates of the present invention comprise, or consist of, a plurality of sulfated GAG polymer chains linked via a linking agent. In some embodiments, polymer conjugates of the present invention comprise, or consist of, a plurality of sulfated GAG polymer chains and at least one additional polymer linked via a linking agent. In some embodiments, polymer conjugates of the present invention comprise, or consist of, a plurality of sulfated GAG polymer chains and at least two additional polymers linked via a linking agent. In some embodiments, polymer conjugates of the present invention comprise, or consist of, a plurality of sulfated GAG polymer chains and at least three additional polymers linked via a linking agent. In some embodiments, including the embodiments described in this paragraph, the sulfated GAG is chondroitin sulfate. In some embodiments, including the embodiments described in this paragraph, an additional polymer is a sulfated GAG other than chondroitin sulfate. In some embodiments, including the embodiments described in this paragraph, an additional polymer is a non-sulfated GAG. In some embodiments, including the embodiments described in this paragraph, an additional polymer is hyaluronic acid (HA) or carboxymethylcellulose (CMC).

It will be appreciated that polymer conjugates of the present invention will generally have higher (e.g., increased) molecular weight compared to an individual GAG polymer chain, but do not form a gel with an extended crosslinking network. In some embodiments, polymer conjugates of the present invention have a molecular weight in a particular range as compared with nonlinked sulfated GAG used as starting material (e.g., polymer conjugates having 3× to 100× or more the molecular weight of an individual, non-linked sulfated GAG starting material). In some embodiments, polymer conjugates of the present invention are branched multi-chained conjugates having a molecular weight in a particular range (e.g., 3× to 100× or more that of an individual, nonlinked sulfated GAG starting material). In some embodiments, polymer conjugates of the present invention are bottlebrush-like multi-chained conjugates having a molecular weight in a particular range (e.g., 3× to 100× or more that of an individual, nonlinked sulfated GAG starting material). In some embodiments, polymer conjugates of the present invention have a molecular weight in a range between about 3× to 100×, 3× to 75×, 3× to 50×, 3× to 25×, 5× to 100×, 5× to 75×, 5× to 50×, and 5× to 25× that of an individual, nonlinked sulfated GAG starting material. In some embodiments, polymer conjugates of the present invention have a molecular weight in a range of 5× to 25× that of an individual, nonlinked sulfated GAG starting material. Water soluble polymers with very high molecular weights have been achieved. For example, crosslinked sulfated GAGs having molecular weights greater than 500K, 600K, 700K, 800K, 900K, 1 million, 1.5 million, 2 million, 2.5 million or more have been achieved.

In some embodiments, polymer conjugates of the present invention are soluble in aqueous solution or saline. In some embodiments, a polymer conjugate of the present invention comprises a plurality of sulfated glycosaminoglycan (GAG) polymer chains, wherein each sulfated GAG is linked to one or more sulfated GAG polymer chains via a linker agent, and wherein the polymer conjugate is soluble in aqueous solution and has a molecular weight that is 3× to 100× that of an individual, nonlinked sulfated GAG.

Without wishing to be bound by any particular theory, polymer conjugate variations include but are not limited to varying length, sulfation pattern, molecular weight, chemical composition, and the like. These variations, which may be controlled using the methods provided herein, can affect the conformation, molecular weight, hydrating, mechanical, and cell signaling functions of the polymer conjugate.

Linker Agent

The skilled artisan will be familiar with types of direct linker agents that are appropriate for linking GAG polymers and other polymers used in accordance with the present invention. It will be appreciated that the terms "linking agent", "linker agent", "cross-linker" and "linker" are interchangeable, with the understanding that the linker is a portion of the conjugate derived from reaction with a linker agent.

In some embodiments, a linker agent is bifunctional. In some embodiments, the linker agent is not polymeric. For example, a polymeric linker is characterized by a repeating unit. In some embodiments, a linker agent is only polymeric where a monomeric unit repeats 10 or fewer times. In some embodiments, a linker agent is only polymeric where a monomeric unit repeats or fewer times. In some embodiments, a linker agent has a molecular weight of less than about 150 Da, 200 Da, 250 Da, 300 Da, 350 Da, 400 Da, 450 Da, 500 Da, 600 Da, 700 Da, 800 Da, 900 Da, or 1000 Da. In some embodiments, a linker agent is not polymeric and is less than about 150 Da, 200 Da, 250 Da, 300 Da, 350 Da, 400 Da, 450 Da, 500 Da, 600 Da, 700 Da, 800 Da, 900 Da, or 1000 Da. In some embodiments, a linker agent is not polymeric and is less than about 1000 Da. In some embodiments, a linker agent is not polymeric and is less than about 500 Da. In some embodiments, a linker agent is not polymeric and is less than about 250 Da. In some embodiments, a linker agent is not polymeric and is less than about 200 Da. In some embodiments, a linker agent is not polymeric and is less than about 150 Da. In some embodiments, a linker agent is not polymeric and is less than 150 Da, 200 Da, 250 Da, 300 Da, 350 Da, 400 Da, 450 Da, 500 Da, 600 Da, 700 Da, 800 Da, 900 Da, or 1000 Da.

In some embodiments, a linker agent is selected from the group consisting of divinylsulfone (DVS), diepoxides, epichlorohydrin (Epi), butanedioldiglycidyl ether (BDDE), and a combination thereof. In some embodiments, a linker agent is epichlorohydrin (Epi). In some embodiments, a linker agent is butanedioldiglycidyl ether (BDDE). In some embodiments, a linker agent is a biscarbodiimide. In some embodiments, a linker agent is phenylene-bis(ethyl carbodiimide). In some embodiments, a linker agent is 1,1'-carbonyldiimidazole. In some embodiments, a linker agent is divinylsulfone (DVS).

In some embodiments, a linker agent is bromoacetic NHS ester, 6-(iodoacetamido)caproic acid NHS ester, maleimidoacetic acid NHS ester, maleimidobenzoic acid NHS ester, or MNICCH (4-(maleimidomethyl) cyclohexane-1-carboxyl hydrazide).

In some embodiments, a linker is a peptidic fragment comprising from 2 to about 20 amino acyl residues, a linear or branched chain alkyl or aryl carboxylic ester, or a $C_{1-20}$ saturated or unsaturated, straight or branched, hydrocarbon chain, wherein one or more methylene units of the linker are optionally and independently replaced by cyclopropylene, —CHOH—, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, or —C(=NR)—.

In some embodiments, a linker or linker agent contains a short poly(alkyleneoxide) chain. In some embodiments, a linker or linker agent is a short poly(ethyleneoxide) chain with epoxide groups at both ends, such as poly(ethylene glycol) diglycidyl ether.

Preferred linkers are water-soluble and are characterized by moieties that react with nucleophilic groups, such as a hydroxy group pendant on a GAG and an amine presented on a modifier.

Sulfated GAG

In some embodiments, a sulfated GAG for use in accordance with the present invention is selected from the group consisting of chondroitin sulfate, heparan sulfate, dermatan sulfate, keratan sulfate, heparin, and combinations thereof. In some embodiments, a sulfated GAG is chondroitin sulfate. Chondroitin sulfate consists of repeating disaccharide units of N-acetylgalactosamine (GalN) and glucuronic acid (GlcN). In some embodiments, chondroitin sulfate can have over 100 sugars, each of which can be independently sulfated in variable positions and quantities (e.g., chondroitin sulfate A, C, D, and E). In some embodiments, the molecular weight of a sulfated GAG may be greater than about 1,000

Da, 5,000 Da, 10,000 Da, Da, 20,000 Da, 30,000 Da, 40,000 Da, 50,000 Da, 100,000 Da, or a range including any two of these numbers. In some embodiments, the molecular weight of chondroitin sulfate may be greater than about 1,000 Da, 5,000 Da, 10,000 Da, 15,000 Da, 20,000 Da, 30,000 Da, 40,000 Da, 50,000 Da, 100,000 Da, 200,000, Da or a range including any two of these numbers. Sulfated GAGs are commonly obtained from natural sources but may be provided by non-animal or synthetic sources.

Modified GAGs

In some embodiments, polymers conjugates of the present invention can be prepared by using modified GAGs, wherein at least one modifier has been introduced to at least one polymer GAG chain. As described above, GAGs have numerous hydroxyl and carboxyl functionalities along the chain. In addition, the reducing end of the GAG provides a single and unique chemical functionality. In order to extend and enhance the therapeutic benefit of the novel compositions described in this invention, the present invention encompasses the recognition that a modifier may be introduced onto the GAG chains prior to (or after) reaction with a linking agent. Practicing the methods of this invention with chemically modified GAGs, or GAG glycoconjugates, will provide high molecular weight proteoglycan mimics with the additional benefits endowed by modifier. For example, a sulfated GAG bearing a peptide with affinity for collagen-I, collagen-II, other collagen isoforms, elastin, integrin receptors, or other ECM components or cell surface proteins including but not limited to galectins will enable more specific binding of the proteoglycan mimic to the target biomolecule. The literature has described several examples of covalent modification of GAGs, and suitable chemistries for such modifications are known to the skilled artisan.

In some embodiments, sulfated GAG may be modified along the GAG polymer chain. In some embodiments, a modifier may be introduced onto a sulfated GAG prior to linking a GAG chain backbone with a linking agent by various methods known to one of skill in the art. In some embodiments, a modifier may be introduced onto a sulfated GAG at its reducing end using reducing end chemistry familiar to the skilled artisan (e.g., reductive amination).

In some embodiments, a sulfated GAG is modified via carboxyl groups along the GAG polymer chain. In some embodiments, a carboxyl group is subjected to peptide coupling conditions to form an amide bond, thereby introducing a modifier. Suitable peptide coupling conditions are well known in the art and include those described in detail in Han et al., Tetrahedron, 60, 2447-67 (2004), and in VR Pattabiraman et. al., Nature, 480, 471-479 (2011), the entirety of which is hereby incorporated by reference. In some embodiments, suitable peptide coupling conditions comprise a peptide coupling reagent selected from a carbodiimide or triazole activating reagent, in the presence of a base such as DIEA or other bases familiar to one skilled in the art. In certain embodiments, the peptide coupling conditions include the addition of HOBt, HOAt, DMAP, BOP, HBTU, HATU, BOMI, DCC, EDC, IBCF, or a combination thereof. In some embodiments, a peptide coupling agent is selected from a triazine activating agent such as 4-(4,6-dimethoxy-1,3,5-triazin-2-yl)-4-methylmorpholinium chloride (DMTMM).

In some embodiments, a soluble high molecular weight sulfated GAG composition may be prepared with polymers that have been chemically substituted with groups to enhance their performance in their intended applications. In some embodiments, such modifiers are substituted randomly along a GAG polysaccharide chain, or only at the reducing end of the chain. In some embodiments, provided polymer conjugates comprise a sulfated GAG such as chondroitin sulfate (ChS) substituted with a peptide modifier known to have strong affinity for a component of the ECM (e.g., collagen, elastin). In other embodiments, provided polymer conjugates comprise a sulfated GAG substituted with an antioxidant modifier or other molecule to enhance its therapeutic benefit. Peptide conjugation is well known in the art as a means of adding biological recognition and function to synthetic polymers and biomaterials. Many short peptide motifs have been identified and utilized in biomaterials applications that can be useful in the formation of GAG conjugates for this invention. Many of these peptides are derived from natural proteins having the desired affinity for a given target biomolecule.

In some embodiments, provided polymer conjugates comprise a sulfated GAG that is substituted with an integrin-binding modifier. Most well-known are the peptide motifs for binding to cell surface integrins are derived from fibronectin: GRGDS (SEQ ID NO: 1), PHSRN (SEQ ID NO: 2), REDV (SEQ ID NO: 3), and LVD. These peptides and their derivatives have affinity for cell surface integrins and have been covalently bound to biomaterials matrices to immobilize cells. Integrin-binding peptides derived from laminin have also been used to attract cells into biomaterials: YIGSR (SEQ ID NO: 4), GIIFFL (SEQ ID NO: 5), IKVAV (SEQ ID NO: 6), their derivatives, and many others.

In some embodiments, provided polymer conjugates comprise a sulfated GAG that is substituted with a collagen-binding agent. There are several peptides known to bind to collagen surfaces. Some have been derived from Decorin: SYIRIADTNITGC (SEQ ID NO: 7) (known as dc-13), LRELHLNNN (SEQ ID NO: 8) (IS-6) and LHERHLNNN (SEQ ID NO: 9). Another well-known collagen-binding peptide is [GPO]7, a 7-mer repeat of the Glycine-Proline-Hydroxyproline collagen motif has helicogenic affinity to fibrillar collagen. The peptide GLRSK-SKKFRRPDIQYPDA (SEQ ID NO: 10) is described in U.S. Pat. No. 9,133,246 B2, where it was used as part of a fusion protein targeted to collagen. U.S. Pat. No. 9,200,039 B2 describes the collagen binding peptide RRANAALKAGE-LYKSILYGC (SEQ ID NO: 11) (known as SILY) and WYRGRLGC (SEQ ID NO: 12) as well as several other examples. In addition, U.S. Pat. No. 8,846,003 B2 describes peptides with specificity for binding at collagen-III surfaces such as: KELNLVYTGC (SEQ ID NO: 13) and GSITTI-DVPWNVGC (SEQ ID NO: 14). Several cyclic peptides with affinity for collagen are described in U.S. Pat. No. 8,034,898 B2 including: WHCYTYFPHHYCVYG (SEQ ID NO: 15); GWHCYTYFPHHYCTYG (SEQ ID NO: 16); AWHCYTYFPHHYCVYG (SEQ ID NO: 17); LWHCYTYFPHHYCVYG (SEQ ID NO: 18); YWHCYTYFPHHYCVYG (SEQ ID NO: 19).

In some embodiments, provided polymer conjugates comprise a sulfated GAG that is substituted with an hyaluronan binding modifier. Peptides with affinity for binding to hyaluronan in the ECM are described in U.S. Pat. No. 9,200,039 B2. These include GAHWQFNALTVRGGGC (SEQ ID NO: 20) (known as GAH) and other examples.

Preferably, polymer conjugates in accordance with the invention comprise at least one sulfated GAG polymer chain that is substituted with at least one glycan ligand for galectins, for example a sulfated GAG polymer chain comprising at least one β-galactose residue (e.g. (3-galactoside).

In some embodiments, a provided polymer conjugate comprises any of the above-described peptides or glycans as a modifier.

Typically, a modifier is added to the soluble polymer conjugate after crosslinking GAGs. It has been surprisingly discovered that adding the modifier after crosslinking is substantially complete results in improved polymer conjugates.

Additional Polymers

In some embodiments of provided polymer conjugates, sulfated GAGs are directly conjugated with other polymers and biomolecules. In some embodiments, hyaluronic acid (HA) or carboxymethyl cellulose (CMC) are incorporated to form a hybrid high molecular weight soluble polymer composition. In some embodiments, sulfated GAGs may be directly conjugated together with other polymers and biopolymers with molecular weights greater than about 250 kDa, 300 kDa, 350 kDa, 400 kDa, 450 kDa, 500 kDa, 1,000 kDa, or a range including any two of these numbers.

Methods of Preparing GAG Polymer Conjugates

As described above, polymer conjugates of the invention are synthesized by an appropriate selection of synthetic reagents and methods. The discussion below is offered to illustrate certain of the diverse methods available for use in assembling the polymer conjugates of the invention. However, the discussion is not intended to limit the scope of reactions or reaction sequences that are useful in preparing the compounds of the present invention.

Scheme A as illustrated below depicts a sulfated GAG (e.g., chondroitin sulfate) and various locations in which a linker agent (e.g., DVS) may be attached:

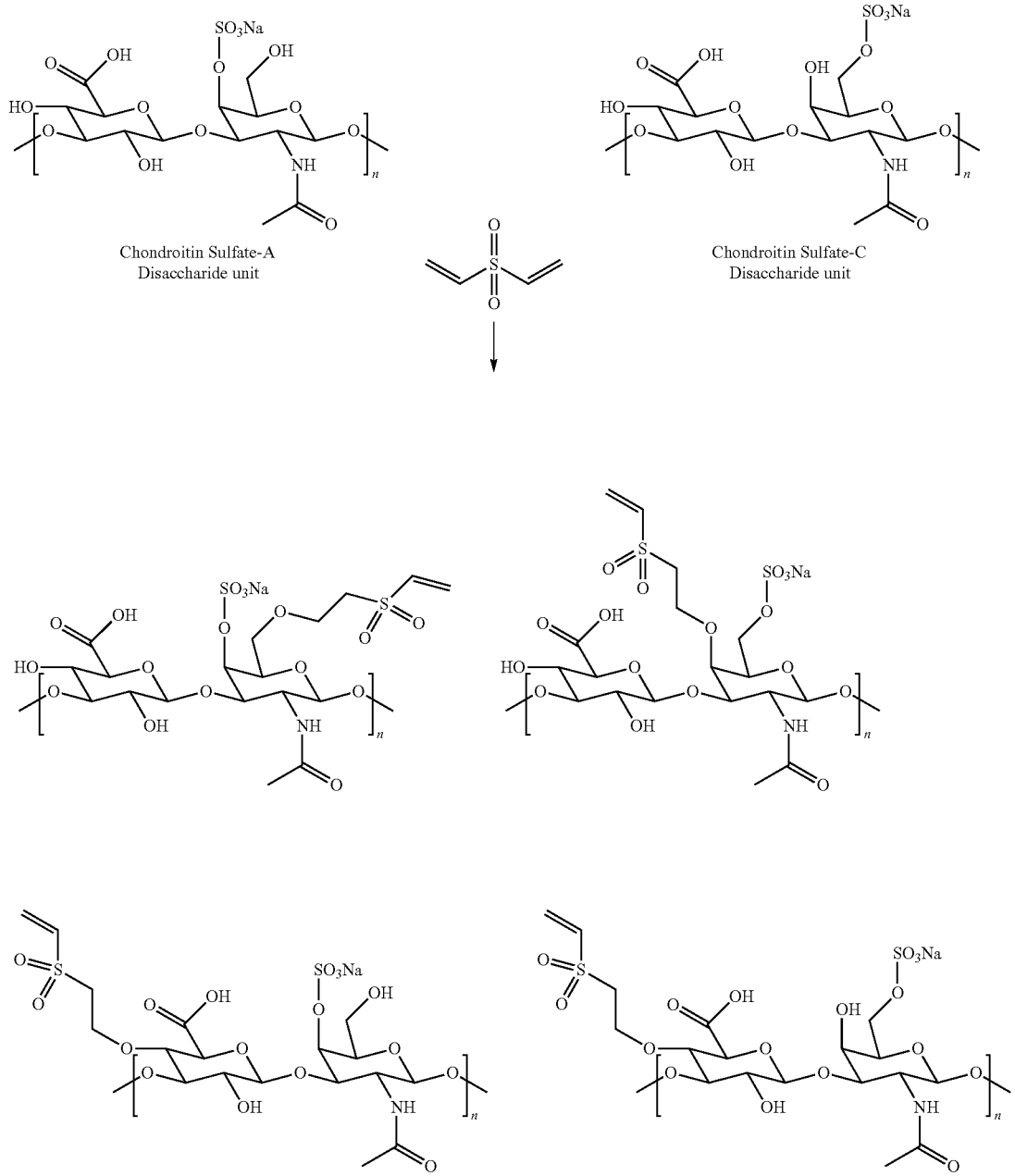

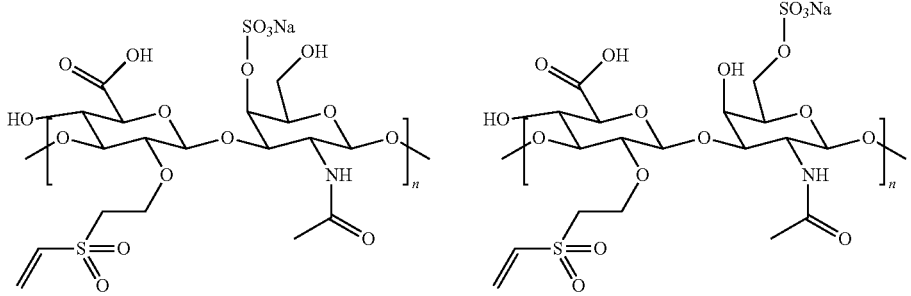

Scheme B as illustrated below depicts an example of a sulfated GAG reacted with a second sulfated GAG with a bound linker agent (DVS) to form a polymer conjugate:

The present invention provides, among other things, methods for preparing polymer conjugates where the predominant product is a sulfated GAG polymer conjugate

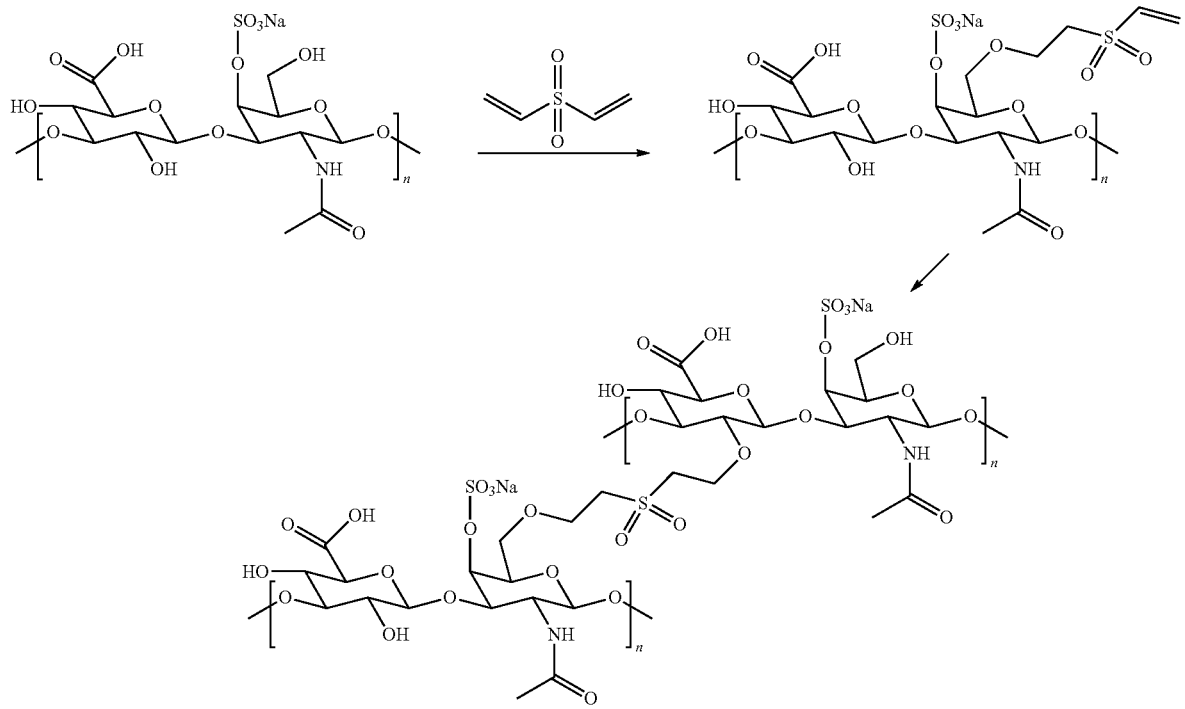

Applicant has observed that, under conditions where the sulfated GAG is present in high concentration, a strong clear gel may be formed rapidly. For example, using a commercial bovine sourced chondroitin sulfate material of Mw=14,000 Da, a hydrogel can be formed within 1-2 hours after addition of DVS in 0.1 N NaOH solution when the chondroitin sulfate is at concentrations greater than 8 wt % (8 g polymer contained in 100 g of solution) and sufficient DVS is used.

Various combinations of the DVS/OH ratio and polymer concentration can be expressed as the weight % of polymer in solution. In some combinations, gels are formed and in others, gels are not formed. In addition, it is possible to quench a reaction prior to formation of a gel. Reaction conditions can be selected such that the reaction mixture remains clear, and conditions in which the reaction becomes hazy or opaque due to the formation of an insoluble, heavily modified polymer derivative.

soluble in aqueous solution. According to one aspect of the present invention, a sulfated GAG is used in methods provided herein at a concentration selected to avoid formation of a gel.

In some embodiments, a sulfated GAG is at concentrations greater than about 1 wt %, 2 wt %, 3 wt %, 4 wt %, 5 wt %, 6 wt %, 7 wt %, or a range including any two of these numbers. In some embodiments, a sulfated GAG is at concentrations less than about 20 wt %, 15 wt %, 12 wt %, 10 wt %, 9 wt %, 8 wt %, 7 wt %, 6 wt %, 5 wt %, 4 wt %, 3 wt %, 2 wt %, or 1 wt %. In some embodiments, a sulfated GAG is at a concentration between the range of 2 wt % and 7 wt %, such as 2 wt % and 5 wt %.

In some embodiments, experiments run in the range between about 8 wt %-16 wt % ChS reveal that the speed of gel formation increases with both the concentration of ChS and the amount of DVS used. For example, when the mole ratio of DVS/hydroxyl group equivalents available on the biopolymer is less than 0.1, a gel is not formed after 90 minutes even for higher concentration solutions (10-12 wt %) of ChS. Thus, a DVS/hydroxyl mole ratio can be less than about 1.0, 0.9, 0.8, 0.7, 0.6, 0.5, 0.4, 0.3, 0.2, 0.1, 0.05, 0.01 or a range including any two of these numbers. Typically, higher mole ratios can be used with lower sulfated GAG concentrations.

In some embodiments, when these reactions were carried out under conditions where the DVS/hydroxyl ratio was systematically increased, it was observed that the speed of gel formation was hastened. Moreover, it was found that when the DVS/hydroxyl levels were high (near or above 1.0), some reactions became cloudy or even formed a white solid precipitate. Characterization of this insoluble product by NMR spectroscopy and found it to be a chondroitin sulfate derivative highly substituted with vinyl sulfone groups. The processes of the invention are typically carried out under conditions that avoid gel formation and maintain a water-soluble polymer conjugate.

"Branched" Polymer Conjugates

In some embodiments, a polymer conjugate of the present invention has branched architecture. In some embodiments, a sulfated GAG is reacted with a linking agent under conditions where the GAG concentration and the molar ratio of linking agent to GAG have been selected to provide a soluble branched polymer rather than an extended crosslinked network. In some embodiments, a linker agent is DVS and the DVS/hydroxyl ratio is between the range of about 0.01 to 0.6. In some embodiments, the DVS/hydroxyl ratio is 0.01, 0.05, 0.1, 0.2, 0.3, 0.4, 0.6, or a range including any two of these numbers.

In certain embodiments, the present invention provides a method of preparing polymer conjugates comprising the steps of: i) providing sulfated GAG in aqueous solution at a concentration of about 2 wt %-20 wt %; and ii) contacting the sulfated GAG with a linking agent, wherein the molar ratio of GAG hydroxyl groups to linking agent is less than that required for gel formation to form a soluble branched polymer. In some embodiments, a sulfated GAG in step i has a molecular weight from 10,000 Da to 100,000 Da. In some embodiments, the molar ratio of GAG hydroxyl groups to linking agent (e.g., DVS/hydroxyl ratio) is from 0.01 to 0.6. In some embodiments, a sulfated GAG in step I has a molecular weight from 5,000 Da to 200,000 Da, such as from 10,000 Da to 100,000 Da and a molar ratio of GAG hydroxyl groups to linking agent (e.g., DVS/hydroxyl ratio) from 0.01 to 0.6.

In some embodiments, a sulfated GAG is reacted with a direct linking agent under conditions where the reaction can be terminated before an extended crosslinked network (e.g., a gel) is formed. In these cases, the linking reaction is easily terminated by the addition of acid (such as HCl) to bring the pH down to a neutral value. Again, a soluble branched polymer is obtained rather than an extended crosslinked network. In some embodiments, the reaction occurs for a certain amount of time before the reaction is terminated. In some embodiments, the reaction occurs for about 1 to 120 minutes. In some embodiments, the reaction occurs for about minutes. In some embodiments, the reaction occurs for about 40 minutes. In some embodiments, the reaction occurs for about 90 minutes.

In some embodiments, a branched polymer conjugate has a molecular weight greater than about 15,000 Da, 20,000 Da, 30,000 Da, 40,000 Da, 50,000 Da, 100,000 Da, 200,000 Da, 300,000 Da, 400,000 Da, 500,000 Da, 1,000,000 Da, or more or a range including any two of these numbers.

"Bottlebrush-like" Polymer Conjugates

In some embodiments, a polymer conjugate of the present invention has bottlebrush-like architecture. In some embodiments, a sulfated GAG is reacted with a linking agent under conditions where reactants are sequentially introduced. In some embodiments, this staged addition of reactants can significantly affect the molecular architecture and properties of the product. For example, in a 1-pot procedure, a small portion of a sulfated GAG can be activated with a linking agent in dilute solution to form an intermediate multivalent reactive core polymer. Subsequent addition of an excess of the same or different sulfated GAG results in formation of a soluble, high molecular weight sulfated GAG composition with a bottlebrush-like architecture.

Thus, in some embodiments the present invention provides a method of preparing polymer conjugates via sequential introduction of the sulfated GAG in a single reaction, comprising the steps of: i) providing a sulfated GAG; and ii) reacting the sulfated GAG with a linking agent under conditions where a small portion of the sulfated GAG is reacted with the full portion of linking agent; and iii) adding the remaining portion of sulfated GAG to form a soluble conjugate with bottlebrush-like architecture.

In some embodiments, a high molecular weight core polymer capable of direct reaction with a linking agent (e.g., CMC, HA) is reacted in the initial step of the 2-stage synthetic procedure. A sulfated GAG may then be introduced to react with the modified core polymer forming a bottlebrush-like polymeric composition in a 1-pot procedure.

In some embodiments, the present invention provides a method of preparing polymer conjugates comprising the steps of: i) activating a core polymer with a linking agent in dilute solution to form an intermediate multivalent reactive core polymer; and ii) adding an excess of a sulfated GAG to form a soluble bottlebrush-like polymer. In certain embodiments, step i comprises activating a core polymer with a linking agent under conditions where a small portion of the core polymer is reacted with the full portion of linking agent. In certain embodiments, step i comprises activating a sub stoichiometric amount of a core polymer (i.e., an excess of linking agent over polymer hydroxyl groups) with a linking agent in dilute solution to form an intermediate multivalent reactive core polymer. In some embodiments, the core polymer of step i is a sulfated GAG identical to that added in step ii. In some embodiments, the core polymer of step i is a sulfated GAG different from that added in step ii. In some embodiments, the core polymer of step i is not a sulfated GAG. In certain embodiments, the core polymer in step i is carboxymethylcellulose. In certain embodiments, the core polymer in step i is hyaluronic acid.

In some embodiments, a provided polymer conjugate is prepared in a 2-step reaction in which the core polymer is first functionalized with a linking agent in dilute solution and is then isolated by precipitation or other means. The intermediate core polymer modified with the linking agent can be characterized and/or purified. Subsequent reaction of this intermediate core polymer in a second reaction with a sulfated GAG in concentrated solution provides a soluble bottlebrush-like polymeric composition.

Thus, in some embodiments, the present invention provides a method of preparing polymer conjugates comprising the steps of: i) functionalizing a core polymer with a linking agent in dilute solution to form an intermediate core polymer; ii) isolating the intermediate core polymer; and iii)

reacting the intermediate core polymer with a sulfated GAG in concentrated solution to form a soluble bottlebrush-like polymer.

In some embodiments, a bottlebrush-like polymer conjugate has a molecular weight greater than about 15,000 Da, 20,000 Da, 30,000 Da, 40,000 Da, 50,000 Da, 100,000 Da, 200,000 Da, 300,000 Da, 400,000 Da, 500,000 Da, 1,000,000 Da, 2,000,000 Da or more or a range including any two of these numbers.

In the process according to the invention, the polymer conjugate, e.g., the bottlebrush-like and/or branched polymer conjugate, is characterized by reactive groups or moieties resulting from incomplete reaction of the linker. For example, where divinyl sulfone (DVS) is used as the linking agent, the polymer conjugate is characterized by unreacted vinyl moieties. Given the propensity of the GAGs to react with DVS and, for example, form stiff gels, the formation of water-soluble polymer conjugates with yet unreacted vinyl groups was surprising.

The presentation of the unreacted vinyl groups can be exploited. The process includes the subsequent addition of a modifier that is capable of reacting with the reactive groups to form a covalent bond. The subsequent addition of the modifier has at least two benefits. First, it results in quenching the remaining reactive groups to avoid unintentional gelling during storage or covalent reaction on use. Second, it can impart a desirable biological activity on the polymer conjugate, such as targeting, as described above.

Characterization Techniques

As described above, in some embodiments, polymer conjugates of the present invention are soluble in aqueous solution. Such conjugates are in contrast to known GAG polymer conjugates that are gels having extended crosslinked networks. While the skilled person can differentiate between materials that are gels and those that are not gels, for the avoidance of doubt, it is noted that for polymerization in homogeneous solution, the formation of an extended crosslinked network will be characterized by a loss of solution characteristics. For example, the reaction mixture will no longer flow, and when the gel is added to a large volume of water it may swell, but it will not dissolve. Such gels take on the properties of a solid, or viscoelastic material. In addition, such gels have viscoelastic properties that can be quantified using rheometry. For example, many strong gels have a storage modulus (G') that is greater than its loss modulus (G").

In some embodiments, provided polymer conjugates will maintain solution flow properties when dissolved in water. In some embodiments, provided polymer conjugates will have molecular weight distributions and degree of branching that will be characteristic of the method of synthesis, and will be reproducible from batch to batch. In some embodiments, provided polymer conjugates are characterized in that a clear viscous fluid, and not a gel, is observed during manufacture of provided polymer conjugates. In some embodiments, polymer conjugates are a clear viscous fluid in aqueous solution.

Characterization of provided polymer conjugates may be provided by gel permeation chromatography (GPC) and dynamic light scattering (DLS). In some embodiments, parameters related to flow such as viscosity or modulus may be determined by viscometry and rheology.

Hydrodynamic radius (Rh) is determined by DLS and is directly related to molecular weight and architecture (type/degree of branching). In some embodiments, an enhancement or increase of Rh over that of the starting material will be achieved. In some embodiments, polymer conjugates of the present invention will have an increased hydrodynamic radius compared to that of a reference. In some embodiments, aggrecan may be a reference used to model an upper limit for both molecular weight and Rh. In some embodiments, starting material (e.g., non-linked sulfated GAG) may be used as a reference.

DLS is a convenient method for direct determination of the size of polymers in solution (Rh), however it does not directly measure molecular weight. Knowing the hydrodynamic radius allows for estimation of molecular weight. DYMANICS® software (Wyatt technologies) uses a shape model to estimate Mw from Rh. This calculation can be done after input of a general polymer architecture model: globular, coiled, branched.

Purification of Polymer Conjugates

In some embodiments, polymer conjugates may be purified by methods known to those of skill in the art. In some embodiments, polymer conjugates may be purified by dialysis. In some embodiments, polymer conjugates may be purified by tangential flow filtration. In some embodiments, polymer conjugates may be precipitated from a crude reaction product. In some cases, the polymer conjugates may be precipitated from the reaction mixture, collected, redissolved in water and precipitated again. Several redissolution/precipitation cycles may be performed. In embodiments, the polymer solution can be microfiltered, for example, passed through a 0.2 micron filter.

Methods of Use

Injuries to soft tissue, for example, vascular, skin, or musculoskeletal tissue, are quite common. Surgical approaches to correct soft tissue defects and or damage in the body generally involve the implantation of structures made of biocompatible, inert materials that attempt to replace or substitute for the defective function. Implantation of nonbiodegradable materials results in permanent structures that remain in the body as a foreign object. Implants that are made of resorbable materials are suggested for use as temporary replacements where the object is to allow the healing process to replace the resorbed material. However, these approaches have met with limited success for the long-term correction of structures in the body.

Thus, the invention includes methods of treating soft tissue comprising contacting the soft tissue with a polymer conjugate described herein.

As a person ages, facial rhytids (wrinkles) and folds develop in response to the loss of facial fat and the decrease of the skin elasticity. The skin loses shape and acute wounds take longer to heal and scar more easily. Physicians have over the years tried various methods and materials to combat the facial volume loss of the soft tissue of the face. Scientists and physicians are constantly searching for the ideal dermal filler.

Soft tissue conditions further include, for example, conditions of skin (e.g., scar revision or the treatment of traumatic wounds, severe burns, skin ulcers (e.g., decubitus (pressure) ulcers, venous ulcers, and diabetic ulcers), and surgical wounds such as those associated with the excision of skin cancers); vascular condition (e.g., vascular disease such as peripheral arterial disease, abdominal aortic aneurysm, carotid disease, and venous disease; vascular injury; improper vascular development); conditions affecting vocal cords; cosmetic conditions (e.g., those involving repair, augmentation, or beautification); muscle diseases; conditions of connective tissues such as tendons and ligaments, including but not limited to a periodontal ligament and anterior cruciate ligament; and conditions of organs and/or fascia (e.g., the bladder, intestine, pelvic floor).

Degenerated and damaged soft tissues of the musculoskeletal system cause and increase the risk of medical complications resulting in intense pain and restricted motion. For example, degenerated and damaged soft tissues of the spine represent the major source of back pain for millions of people around the world. Soft tissue degeneration of the ligaments and intervertebral discs also increase the risk of damage to and back pain from local spinal joints, including: zygapophysical (facet), costovertebral, sacroiliac, sacral vertebral and atlantoaxial joints.

In some embodiments, polymer conjugates of the present invention are for use in medicine. In some embodiments, polymer conjugates of the present invention are for use in treating a disease, disorder, or condition associated with a soft tissue in a mammal. In some embodiments, polymer conjugates of the present invention are for use in treating diseases, disorders, or conditions associated with soft tissue defects and/or disorders, where administration of a conjugate of the present invention to the soft tissue site results in functional restoration of the soft tissue, in whole or in part.

In some embodiments, soft tissue treated in accordance with the present invention is selected from the group consisting of intervertebral disc, skin, heart valve, articular cartilage, cartilage, meniscus, fatty tissue, craniofacial, ocular, tendon, ligament, fascia, fibrous tissue, synovial membrane, muscle, nerves, blood vessel, and any combination thereof. In some embodiments, polymer conjugates of the present invention are for use in dermal, orthopedic, urology, wound repair, and topical cosmetics.

In some embodiments, polymer conjugates of the present invention are for use in treating a disease, disorder, or condition associated with degradation of the ECM in a mammal. In some embodiments, polymer conjugates of the present invention are for use in treating diseases, disorders, or conditions associated with ECM defects and/or disorders, where administration of a conjugate of the present invention to the ECM results in functional restoration of the ECM, in whole or in part.

In some embodiments, polymer conjugates of the present invention provide a method of delaying the onset of (e.g., preventing) soft tissue loss. In some embodiments, polymer conjugates of the present invention provide a method for augmenting soft tissue. In some embodiments, polymer conjugates of the present invention provide a method for cosmetic augmentation. In some embodiments, polymer conjugates of the present invention provide methods of treating a subject suffering from age related degeneration of connective tissues or diseases related to the degeneration of connective tissues.

In some embodiments, polymer conjugates of the present invention are for use in acute wound healing. In some embodiments, polymer conjugates of the present invention are for use in regenerative medicine.

Interstitial cystitis (IC), or bladder pain syndrome (BPS), is a chronic disease affecting 4 to 12 million people in the United States, mostly women. IC/BPS is characterized by frequent urination, increased urgency, and pain associated with bladder filling. Therefore, polymer conjugates of the present invention are preferably for use in treating the damaged urothelium of the bladder found in patients suffering from painful bladder syndrome or interstitial cystitis. In some embodiments, the polymer is preferably administered to the bladder via intravesical instillation. The present invention also contemplates treating patients with radiation-induced cystitis, bacterial cystitis, cystitis associated with chemotherapy or cystitis induced by ketamine.

Although the etiology is unknown, and without being limited to any particular theory, one leading theory proposes that bladder pain symptoms originate from a loss of the tight impermeable barrier at the luminal bladder surface leading to activation of visceral afferent fibers innervating the urothelium. The "umbrella cells" that comprise the luminal cell layer responsible for bladder impermeability can be absent or less than fully differentiated, the normal layer of glycosaminoglycans (GAGs) on the surface is compromised and tight junction protein expression is altered. Parsons demonstrated that IC patients showed a significantly higher absorption of urea instilled into the bladder than did controls, and Hurst showed unambiguously using MIII that the urothelium of IC/BPS patients have significantly greater permeability than normal controls. What is unclear is how the bladder loses its impermeability. Evidence suggests it can occur both endogenously through neural connections, possibly modulated by inflammatory cells, and from substances in the urine or loss of cation scavengers.

Therapeutic options for IC/BPS are limited despite the wide variety of agents that have been tried. Some success has come through the restoration of urothelial impermeability through GAG-replenishment therapy. GAG-replenishment involves intravesicular administration of chondroitin sulfate and hyaluronan, either singly or together, heparin, or pentosan polysulfate (ELMIRON®). Unfortunately, response rates rarely exceed 50% to 60%. The limited efficacy of current GAG-replacement therapy may be explained by the inability of these agents to replicate the native GAG layer of the urothelium. The urothelial GAG layer is composed of proteoglycans (PGs), mostly biglycan and perlecan. PGs are glycoproteins usually substituted with clusters of sulfated GAG chains, thereby increasing the interactions of these sulfated GAGs with other biomolecules and creating a zone of very high anionic charge. The resulting osmotic pressure ensures very effective hydration for PG-rich tissues and interfaces. Current approaches for GAG-replenishment in IC/BPS provide only linear, single-chain GAGs such as hyaluronic acid, which is non-sulfated, or sulfated GAGs of low MW (<50 kDa) such as chondroitin sulfate. These single chain GAGs are not able to mimic the clustered sulfated GAG environment provided by PGs on the surface of the native urothelium. PGs themselves are not practical therapeutics because they are complex biomolecules difficult to isolate and purify from tissue.

However, the proteoglycan mimic conjugated polymers of the present invention mimic the PG structure by representing a polyvalent array of sulfated GAG chains for binding biological surfaces in a way that is not possible for single, linear GAG chains. For restoring bladder impermeability in IC/BPS, binding to the bladder endothelium is critical, and therefore this polyvalent display of sulfated GAG chains presented by proteoglycan mimic conjugated polymers of the invention represents a significant innovation. Preferably, the proteoglycan mimics of the invention provide targeted treatment of IC/BPS by further functionalization with, for example a glycan ligand for galectin, such as a ligand comprising a β-galactoside. Such polymer conjugates "decorated" with, for example β-galactoside will target galectins present in the bladder epithelium. Therefore, the invention provides method of treating Interstitial Cystitis (IC) in a patient comprising the step of administering to the patient, a polymer conjugate of the invention, and preferably a polymer conjugate of the invention wherein at least one sulfated GAG polymer chain comprises at least one glycan ligand for galectin (e.g., a β-galactoside).

In some embodiments, the treatment of IC/BPS using polymer conjugates of the present invention or any other GAG biopolymer is combined with diagnostic MRI imaging of the bladder comprising the instillation of an appropriate Mill contrast dye such as Gd(DTPA), Gd(DOTA), or other Gd-based Mill contrast agents and observation of pathological bladder permeability as described in the literature [Towner, R. A., Wisniewski, A. B., Wu, D. H., Van Gordon, S. B., Smith, N., North, J. C., . . . Hurst, R. E. (2016). A Feasibility Study to Determine Whether Clinical Contrast Enhanced Magnetic Resonance Imaging can Detect Increased Bladder Permeability in Patients with Interstitial Cystitis. Journal of Urology, 195(3), 631-638. https://doi.org/10.1016/j.juro.2015.08.077]. The invention imagines coupling the use of this diagnostic Gd-based MRI contrast agent with the polymer conjugates of the present invention, or other GAGs for the treatment on IC/BPS specifically in patients who have measurable bladder permeability.

In some embodiments, polymer conjugates of the present invention are for use in treating a degenerated disc. In some embodiments, polymer conjugates of the present invention are for use in a method of administering polymer conjugates into the nucleus of a degenerated disc in order to increase the osmotic potential of the disc. Administration of a material of polymer conjugates into the nucleus of a degenerated disc can restore normal disc height and function. Preferably a polymer conjugate of the invention is administered by direct injection into an intervertebral disc. Such administration can result in whole or partial restoration of the load-bearing and viscoelastic properties of the defective intervertebral disc.

In some embodiments, polymer conjugates of the present invention are for use in osteoarthritis OA of the knee and other joints. OA, also known as degenerative joint disease, is the most common form of arthritis and results from the gradual breakdown of cartilage that accompanies aging. Typically, OA follows trauma or chronic joint injury due to some other type of arthritis such as rheumatoid arthritis. Alternatively, OA can result from overuse of a particular joint. OA most commonly involves the joints of the elbow, fingers, hips, knees, shoulder, wrist, spine, and toes. Clinically, OA is characterized by joint pain, tenderness, limitation of movement, crepitus, and inexorably progressive disability. It can be present in just one of these joints or in all of them. Although most body tissues can make repairs following an injury, it is believed cartilage repair is hampered by a limited blood supply and the lack of an effective mechanism for cartilage re-growth. Preferably, the invention provides methods of administering the polymer conjugates of the invention to a patient suffering from OA. Preferably, the polymer conjugates of the invention may be administered to the patient by direct injection to the afflicted joint. Preferably, the polymer conjugates of the invention may be administered to the patient by direct injection to the afflicted joint in combination with additional viscosupplementation including but not limited to hyaluronic acid (HA)-containing viscosupplements such as EUFLEXXA®, HYALGAN®, ORTHOVISC®, SUPARTZ®, and SYNVISC®.

The polymer conjugates can be used for tissue repair, such as methods and materials for repairing damaged tissue. Any appropriate tissue can be repaired according to the methods provided herein. For example, the tissue can be any tissue for which tissue adhesion presents a problem following surgical repair. In some cases, tissue can be tendon, ligament, muscle, uterine, or abdominal tissue. For example, tissue can be the muscles and tendons of a rotator cuff, and damaged tissue can be a torn rotator cuff. Tendons that can be repaired or replaced by the methods described herein can include, for example, the supraspinatus tendon, infraspinatus tendon, Achilles tendon, tibialis anterior tendon, peroneus longus tendon, peroneus medius tendon, extensor digitorum longus tendons, extensor hallucis longus tendon, flexor digitorum longus tendon, or patellar tendon. Ligaments that can be repaired or replaced by the methods described herein can include, for example, the ulnar collateral ligament, radial collateral ligament, medical collateral ligament, lateral collateral ligament, anterior cruciate ligament, posterior cruciate ligament, anterior or posterior talofibular ligaments, calcaneofibular ligament, talocalcaneal ligament, or posterior talocalcaneal ligament. For example, a polymer conjugate can be contacted to the site of tissue damage. For example, a polymer conjugate can be contacted to the lacerated ends of tendons or ligaments. Contacting can occur prior to, during, or following surgical repair (e.g., suturing) of lacerated tissue. In order to prevent tissue adhesion and seepage of an anti-adhesive between lacerated ends of the tissue, a polymer conjugate can provide an anti-adhesive coating applied either prior to or after implantation, or both prior to and following implantation. With a polymer conjugate contacting the tissue, an anti-adhesive coating can be applied to the surrounding tissue. The benefits of this method provide a passive barrier to prevent anti-adhesive leakage into the wound site and/or can actively promote wound healing and/or can prevent the adhesion of the wounded tissue to surrounding soft tissue during wound healing.

Additional examples of tissue repair or healing include membrane restoration, such as mucosal membranes, for example, associated with the ears, nose and throat or dermis. For example, the invention includes treating acid reflux, mucositis, periodontitis, rhinosinusitis, chronic sinusitis, strep pharyngitis, herpes, otitis, atopic dermatitis, rosacea, psoriasis, eczema, acne, facial erythema, impetigo, burns, tinea corporis, candidiasis, shingles, and the like. The invention also includes ophthalmic delivery. Ocular diseases include eye infections, blepharitis, dry eye, inclusion conjunctivitis, glaucoma, inflammatory ocular conditions and the like. The polymer conjugates of the present invention can be used in conjunction with any known or heretofore unknown method of treating a disc disease or condition in a mammal. Preferably, the subject is a human.

Administration

In some embodiments, polymer conjugates of the present invention may be formulated with one or more excipients, buffers, carriers, stabilizers, preservatives and/or bulking agents. In some embodiments, polymer conjugates of the present invention may be formulated using excipients that are fully biocompatible (i.e., non-toxic). In some embodiments, polymer conjugates of the present invention may be formulated using excipients and are buffered at physiological pH by salts (e.g., sodium phosphate salts).

Polymer conjugates of the present invention may be administered to a soft tissue site in a subject, for the functional restoration thereof, using a variety of methods and in a variety of formulations known in the art. The methods of administration are chosen depending on the condition being treated and the pharmaceutical composition. Administration of polymer conjugates of the invention can be done in a variety of ways, including, but not limited to, cutaneously, subcutaneously, intravenously, orally, topically, transdermally, intraperitoneally, intramuscularly, and intravesically. For example, microparticle, microsphere, and microencapsulate formulations are useful for oral, intramuscular, or subcutaneous administrations. Liposomes and nanoparticles are additionally suitable for intravenous administrations. Administration of the polymer conjugates of the invention may be through a single route or concurrently by several routes. For instance, oral administration can be accompanied by intravenous or parenteral injections.

Preferably, the subject compositions are administered by intravesical instillation. The procedure generally involves inserting a catheter into urinary tract and filling the bladder with a suitable diluent containing the subject composition. Filling may be made by manual infusion or renal pump. Electromotive drug administration can further assist intravesical drug delivery (see for example, Riedl, C. R. et al., J. Endourol. 12: 269-72 (1998); incorporated by reference).

Preferably, the conjugates of the invention are administered by direct injection into the dermis using a small gauge needle or microneedle or microneedle array. The polymer conjugates of the invention as branched biopolymers have the advantage of low viscosity when in solution which facilitates injection through small gauge needles.

In some embodiments, it is preferable that the polymer conjugates of the present invention do not appreciably degrade following administration. In some embodiments, it is preferred that the composition of the invention degrades either rapidly, or slowly, in the tissue. Thus, when administered in the body, polymer conjugates, may be permanent, may be degraded enzymatically, or may be degraded in the presence of a solvent, such as, for example, water.

The methods of the present invention include the determination of optimum doses of the compounds and pharmaceutical compositions for treating IC symptoms, which may be determined in consideration of the results of animal experiments. More specific doses obviously vary depending on the administration method, the condition of the subject such as age, body weight, sex, sensitivity, food eaten, dosage intervals, medicines administered in combination, and the seriousness and degree of the IC. The optimal dose and the administration frequency under a given condition must be determined by the appropriate dosage test of a medical specialist based on these guidelines, and does not constitute undue experimentation for one skilled in the art.

The polymer conjugates of the invention may also be administered using sustained release or long-term delivery methods, which are well known to those skilled in the art. By "sustained release" or "long term release" as used herein is meant that the delivery system administers a pharmaceutically therapeutic amount of polymer conjugate for more than a day, preferably more than a week, and most preferable at least about 30 days to 60 days, or longer. Long term release systems may comprise implantable solids or gels containing the polymer conjugate, such as biodegradable polymers.

The polymer conjugate of the invention may be administered in combination with one or more other drugs (or as any combination thereof). The polymer conjugate of the invention may be usefully combined with another pharmacologically active compound, or with two or more other pharmacologically active compounds, for the treatment of a pain and/or a lower urinary tract symptom (LUTS) associated with IC and/or painful bladder syndrome and/or bladder pain syndrome. For example, the polymer conjugate of the invention may be administered simultaneously, sequentially or separately, in combination with one or more agents selected from:

an opioid analgesic, e.g., morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g., aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g., amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g., chlordiazepoxide, clorazepate, diazepam, flurazepam, lorazepam, oxazepam, temazepam or triazolam;

an $H_1$ antagonist having a sedative action, e.g., diphenhydramine, pyrilamine, promethazine, chlorpheniramine or chlorcyclizine;

a sedative such as glutethimide, meprobamate, methaqualone or dichloralphenazone;

a skeletal muscle relaxant, e.g., baclofen, carisoprodol, chlorzoxazone, cyclobenzaprine, methocarbamol or orphrenadine;

an NMDA receptor antagonist, e.g., dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (—)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g., doxazosin, tamsulosin, clonidine, guanfacine, dexmetatomidine, modafinil, terazosin, indoramin, alfuzosin, silodosin or 4-amino-6,7-dimethoxy-2-(5-methane-sulfonamido-1,2,3,4-tetrahydroisoquinol-2-yl)-5-(2-pyridyl)quinazoline; prazosin;

a tricyclic antidepressant, e.g., desipramine, imipramine, amitriptyline or nortriptyline; an anticonvulsant, e.g., carbamazepine, lamotrigine, topiratmate or valproate;

a tachykinin (NK) antagonist, particularly an NK-3, NK-2 or NK-1 antagonist, e.g. (aR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g, oxybutynin, tolterodine, fesoterodine, 5-hydroxymethyltolterodine, propiverine, trospium chloride, darifenacin, solifenacin, temiverine and ipratropium;

a COX-2 selective inhibitor, e.g., celecoxib, rofecoxib, parecoxib, valdecoxib, deracoxib, etoricoxib, or lumiracoxib;

a coal-tar analgesic, in particular acetaminophen/paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, MIRAXION® or sarizotan;

a vanilloid receptor agonist (e.g., resinferatoxin) or antagonist (e.g., capsazepine);

a beta-adrenergic such as propranolol;

a local anaesthetic such as mexiletine;

a corticosteroid such as dexamethasone;

a 5-HT receptor agonist or antagonist (e.g., pizotifen), and particularly a 5-HTiwiD agonist such as eletriptan, sumatriptan, naratriptan, zolmitriptan or rizatriptan;

a $5\text{-HT}_{2A}$ receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

TRAMADOL (trade mark);

a PDE-5 inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2'1',1:6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-[5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1α,3α,5α)(3-amino-methyl-bicyclo[3.2.0]hept-3-yl)-acetic acid, (3 S,5R)-3-aminomethyl-5-methyl-heptanoic acid, (3 S,5R)-3-amino-5-methyl-heptanoic acid, (3 S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3 S,4S)-(1-aminomethyl-3,4-dimethyl-cyclopentyl)-acetic acid, (3 S,5R)-3-amino-5-methyl-nonanoic acid, (3R,4R,5R)-3-amino-4,5-dimethyl-heptanoic acid and (3R,4R,5R)-3-amino-4,5-dimethyl-octanoic acid; (3S,5R)-3-aminomethyl-5-methyloctanoic acid;

a cannabinoid;

metabotropic glutamate subtype 1 receptor (mGluR1) antagonist;

a serotonin reuptake inhibitor such as sertraline, sertraline metabolite desmethylsertraline, fluoxetine, norfluoxetine (fluoxetine desmethyl metabolite), fluvoxamine, paroxetine, citalopram, citalopram metabolite desmethylcitalopram, escitalopram, d,1-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buproprion, buproprion metabolite hydroxybuproprion, nomifensine and viloxazine (VIVALAN®), especially a selective noradrenaline reuptake inhibitor such as reboxetine, in particular (S,S)-reboxetine; a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, 5-[2-[(1-iminoethyl)-amino]ethyl]-4,4-dioxo-L-cysteine, 5-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3-pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin $E_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methyl-benzenesulfonamide or 4-[(15)-1-({[5-chloro-2-(3-fluorophenoxy)pyridin-3-yl]carbonyl}amino)ethyl]benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870;

a 5-lipoxygenase inhibitor, such as zileuton, 6-[(3-fluoro-5-(4-methoxy-3,4,5,6-tetrahydro-2H-pyran-4-yl)phenoxy-methyl]-1-methyl-2-quinolone (ZD-2138), or 2,3,5-trimethyl-6-(3-pyridylmethyl),1,4-benzoquinone (CV-6504);

a sodium channel blocker, such as lidocaine; or bupivicaine a 5-HT3 antagonist, such as ondansetron;

glycosaminoglycan layer replacer and anti-inflammatory, such as pentosan polysulphate (ELMIRON™);

a beta-3 agonist, such as YM-178 (mirabegron or 2-amino-N-[4-[2-[[(2R)-2-hydroxy-2-phenylethyl]amino]ethyl]phenyl]-4-thiazoleacetamide), solabegron, KUC-7483 (ritobegron or 2-[4-[2-[[(1S,2R)-2-hydroxy-2-(4-hydroxyphenyl)-1-methylethyl]amino]ethyl]-2,5-dimethylphenoxy]-acetic acid) or AK-134;

an anti-histamine, such as hydroxyzine;

a Hz-antagonist, such as cimetidine; or ranitidine silver nitrate;

a steroid;
doxorubicin;
chondroitin sulphate;
disodium chromoglycate;
oxychlorosene (Clorpactin-trade mark); and
an immunosuppressant, such as cyclosporine.

EXAMPLES

The examples below are meant to illustrate certain embodiments of the invention, and not to limit the scope of the invention.

Materials and Methods

Chondroitin sulfate was obtained from Bioiberica, EP Injectable grade (GPC data from supplier: Mn=11,400, Mw=13,700 Da, PDI=1.21). The equivalent weight of the disodium chondroitin sulfate-A structural repeat unit is 503.35 g/equiv. ($C_{14}H_{19}O_{14}SNa_2$), and the hydroxyl equivalent weight is 503.35/3=167.78 g/OH equiv. Divinylsulfone 99% was purchased from ACROS Organics. Carboxymethylcellulose (MW=250 kDa, and 90 kDa, degree of substitution=0.80, 226.16 g/equiv., 113.08 g/OH equivalent) was purchased from Sigma Aldrich.

Protocol for DLS

Dynamic light scattering analysis was performed on a DynaPro Nanostar instrument (Wyatt Technology) using Wyatt's Cyclic Olefin Copolymer disposable micro cuvette. Data were collected at 25° C. with an acquisition time of 10 s and the hydrodynamic radii were averaged over 20 acquisitions. Data were fitted using the DYNAMICS software version 7.5 (Wyatt Technology) to obtain hydrodynamic radius and estimate molar mass.

Example 1: Synthesis of Soluble High MW Chondroitin Sulfate Composition with a Bottlebrush-Like Architecture by the Staged Addition of Reactants in 1-Pot in the Presence of Sodium Chloride (in Stage 1 and 2). Purification of the Product Using an Optimized Tangential Flow Filtration Protocol IA. Reaction Via Staged Addition Sodium chondroitin sulfate (0.306 g, 1.823 mmol equiv. hydroxyl groups) and sodium chloride (85.2 mg, 1.46 mmol) were dissolved in 9.746 g DI water in a 20 mL reaction vessel. A clear colorless solution was obtained. DVS (0.254 g, 216 uL, 2.15 mmol) was added volumetrically with a microliter pipette. After gentle mixing, the solution was clear and colorless. Reaction was initiated by the addition of 1.03 mL of 1.0 N NaOH using a microliter pipette. With the addition of NaOH, the solution immediately became pale yellow in color and remained clear. The reaction is 3.04 wt % in chondroitin sulfate and is 0.1 M in NaOH (pH 13). The reaction was gently mixed on a rotisserie. After 15 minutes, additional sodium chondroitin sulfate was added (0.909 g, 5.42 mmol equiv. hydroxyl groups), and the reaction mixture was agitated on a rotisserie. The reaction solution became more viscous but remained clear and fluid. Two hours after initiation by NaOH, the reaction was quenched by adding 1.03 mL of 1.0 N HCl using a microliter pipette. The clear fluid reaction mixture was added to a vial containing 50 g of PBS and the total weight was brought to 80 g with addition PBS. The diluted reaction mixture was easily filtered through a 0.45 um PVDF syringe filter.

1B. Purification Using Tangential Flow Filtration

A Spectrum Lab KR2i TFF system was used with a 250 ml feed reservoir and a 20-cm hollow fiber filter module containing modified polyethersulfone filter fibers (1 mm diameter, 100 kDa MWCO, 75 cm$^2$ total surface area, part #D02-E100-10-N). The full 80 g portion of the diluted product of Example 11A was loaded into the feed reservoir. The tangential flow filtration was initiated at 200 ml/min flow rate, with flow rate increasing to 300 ml/min keeping the inlet pressure below 25 psig. TFF was run in dialysis mode in which the volume of solution lost to permeate was continuously made up with additional PBS. In this way, the volume of retentate solution remained constant during the filtration procedure as five volumes (400 ml) of permeate was generated. The TFF was then continued in desalting mode by replenishing the feed reservoir with DI water (instead of PBS) and continuing filtration until an additional five volumes of permeate (400 ml) was obtained. The DI water replenishment was then suspended, and the filtration was run in concentration mode to reduce the retentate volume down to approximately 50 mL. The TFF was then stopped and the system was flushed (10 ml DI water) to recover hold-up volume. The purified retentate was then dried by lyophilization for 72 hours, yielding purified product (0.538 g, 45% yield relative to starting chondroitin sulfate weight) as a white fluffy solid.

This example demonstrates that the staged-addition reaction protocol in the presence of sodium chloride provides a soluble polymer, filterable through a 0.45 um membrane, and purified by tangential flow filtration with a 100 kDa MWCO filter. The soluble polymer was obtained in good yield after TFF purification. It is expected to have a molecular weight significantly greater than the starting material, and a branched conformation.

Example 2: Variation of Stage-1 and Stage-2 Chondroitin Sulfate Ratio to Control the Size of the Resulting High MW Chondroitin Sulfate Compositions with Bottlebrush Architecture The procedure of Example-1 was generalized and repeated resulting in several reactions in which the overall chondroitin sulfate and DVS amounts were held constant, but the chondroitin sulfate apportionment between stage-1 and stage-2 was varied. All reactions were run for 120 minutes, then quenched with HCl, diluted, and filtered through a 0.45-micron mPES syringe filter before being purified by TFF with a 100 kDa MWCO filter exactly as was described in Example-1. The dry products were then obtained after lyophilization.

The products of these reactions were characterized using static and dynamic light scattering measurements made with the Wyatt DynaPro Nanostar. The MW determinations for these highly branched materials using the static light scattering function of the NanoStar are qualitative because of their unusual dendritic structure. However, MW results as well as the radius determinations were obtained using identical experimental conditions and instrument settings so that a relative ranking of the polymer sizes could be made. Accurate MW measurements for these materials must be obtained by a more rigorous method such as SEC-MALLS.

The results of this experiment are shown in the following table. The data show that when the total amounts of chondroitin sulfate and DVS were held constant, the molecular weight of the resulting polymer conjugates were strongly affected by the relative portioning of chondroitin sulfate between stage-1 and stage-2. When the proportion of chondroitin sulfate charged to the reaction in stage-1 was increased, larger molecular weight polymers were obtained. This observation is consistent with a mechanism in which a significant amount of molecular weight growth takes place in stage-1 producing a vinyl-sulfone functional, branched chondroitin sulfate composition. Extended network (gel) formation in stage-1 is avoided because the overall concentration of CS at this stage of the reaction remains relatively low. The additional CS added in stage-2 serves to quench the reactive groups on the growing branched chondroitin sulfate composition and build additional molecular weight. Extended network (gel) formation in Stage-2 is avoided because the majority of reactive vinyl sulfone groups are now pendant on the growing branched polymer, and the concentration of free DVS at this stage of the reaction is expected to be relatively low.

| Increasing % of CS in Stage1 gives higher MW product | | | | |
| --- | --- | --- | --- | --- |
| Total CS (% wt) | DVS ratio | Stage1/Stage2 ratio | Radius* (nm) | MW† (kDa) |
| 6 | 0.7 | 60/40 | 16 | 86 |
|  |  | 70/30 | 19 | 104 |
| 8 | 0.5 | 30/70 | 21 | 140 |
|  |  | 50/50 | 52 | >560 |
| 10 | 0.3 | 20/80 | 18 | 190 |
|  |  | 25/75 | 27 | 233 |
|  |  | 30/70 | 49 | 435 |
|  |  | 35/65 | 43 | 420 |
|  |  | 40/60 | 61 | >560 |
| 12 | 0.2 | 20/80 | 28 | 199 |
|  |  | 25/75 | 48 | 559 |

*Hydrodynamic radius measurement from cumulants
†MW estimate from static light scattering data Example 3: Characterization of Soluble High MW Chondroitin Sulfate Compositions with Bottlebrush-Like Architecture by SEC-MALLS The SEC characterization was verified using an independent, ISO 17025 accredited analytical laboratory. Experimental conditions for SEC-MALLS are summarized below.

| Conditions for SEC-MALLS | |
| --- | --- |
| Columns: | Two Agilent PL aquagel-OH Mixed-H columns, 8-μm particle size, 300-mm length × 7.5-mm internal diameter, preceded by PL aquagel-OH guard |
| Mobile phase: | 0.1 molar sodium nitrate, 0.01 molar sodium phosphate monobasic in water, adjusted to 7.0 pH with sodium hydroxide |
| Detector: | Wyatt Technologies HELEOS II multi-angle light scattering detector Wyatt Technologies T-rEX refractive index detector |
| Temperature: | 30° C. (columns and RI detector) |
| Flow rate: | 0.8 mL/min |
| Run time: | 40 minutes |
| Sample prep: | 2 mg/ml in mobile phase, overnight hold, 0.45-micron filter (PVDF) |
| Injection volume: | 100 μL |

For this evaluation materials were prepared using the general 2-stage procedure described in Example-1 but varying several key reaction parameters in order to observe the impact of these parameters on molecular weight. The results shown are the average of two reproducible chromatograms. A critical parameter for molecular weight measurement using light scattering is the specific refractive index increment (dn/dc), which is defined as the change in refractive index of a solution that occurs when the solute concentration is changed. A do/dc value used in this project was 0.1427 mL/g, as found in the literature [Li, L.; Li, Y.; Feng, D.; et. al. Preparation of Low Molecular Weight Chondroitin Sulfates, Screening of a High Anti-Complement Capacity of Low Molecular Weight Chondroitin Sulfate and Its Biologic Activity Studies in Attenuating Osteoarthritis. *Int. Journal of Mol. Science* s2016, 17(10), 1685]. The following table summarizes this result. An analysis of the sodium chondroitin sulfate starting material was included for comparison.

| SEC-MALLS results | | | | | | | |
| --- | --- | --- | --- | --- | --- | --- | --- |
| Total CS (% wt) | DVS ratio | Stage1/Stage2 ratio | Reaction time (min) | Mn | Mw | Mz | Mw/Mn |
| *CS | n.a. | n.a. | n.a. | 11,700 | 13,700 | 16,700 | 1.17 |
| 6 | 0.7 | 60/40 | 60 | 41,300 | 72,600 | 161,000 | 1.76 |
| 10 | 0.3 | 30/70 | 60 | 96,900 | 275,000 | 1,190,000 | 2.84 |
| 10 | 0.3 | 30/70 | 90 | 194,000 | 1,120,000 | 6,870,000 | 5.78 |

*CS = chondroitin sulfate starting material

The results show that the weight-average molecular weight (Mw) for the inventive examples made in a staged-addition procedure have molar masses many times greater than the chondroitin sulfate from which they were made. Although these materials are somewhat polydisperse, the refractive index and light scattering chromatograms showed reasonable peak shapes.

Example 4: Characterization of Soluble High MW Chondroitin Sulfate Compositions with Bottlebrush-Like Architecture by 1H-NMR: The Quantification of Pendant Vinyl Sulfone Groups Branched chondroitin sulfate compositions produced using the procedure described above were characterized using 1H-NMR. In each case the branched high MW chondroitin sulfate compositions were dissolved in D2O (15 mg/ml) and placed in standard 5 mm borosilicate NMR tubes. Proton NMR spectra were collected on a JEOL ECZ 400 Nuclear Magnetic Resonance Spectrometer with a 5 mm Broad Band Probe using automatic tuning and matching, and Delta 5.3 software for data acquisition and processing, as well as MNova software for processing.

It was found that the 1H-NMR spectrum of CS perfectly matched the published spectrum for bovine trachea derived chondroitin sulfate [Mucci, A., Schenetti, L., & Volpi, N. (2000), *1H and 13C nuclear magnetic resonance identification and characterization of components of chondroitin sulfates of various origin*. Carbohydrate Polymers, 41(1), 37-45. https://doi.org/10.1016/S0144-8617(99)00075-2]. In the 1.5-5.0 ppm region, the 1H-NMR spectra of CS and branched high MW chondroitin sulfate compositions are very similar except for two new strong peaks at 3.6 and 4.1 ppm present in the spectrum of the branched high MW chondroitin sulfate composition. These new resonances are expected from the methylene protons of the diethylsulfonyl groups present in branched high MW compositions from the bridging linker groups. Note that this chemical structure is illustrated in reaction SCHEME-B. The methylene signal at 4.1 is attributed to the methylene bound to the sulfone group and the methylene at 3.60 is attributed to the methylene bound to the ether group that was formed in the linking reaction.

The inventors found that as the relative amount of DVS incorporated into the branched high MW chondroitin sulfate composition was increased, the 1H-NMR spectrum indicated a proportional increase in the intensity of the diethylsulfonyl peaks at 4.1 and 3.6. The remaining CS peaks remained unchanged.

Unexpectedly, the inventors also found that in addition to the diethylsulfonyl peaks at 4.1 and 3.6, in some cases the 1H-NMR spectra of branched high MW chondroitin sulfate compositions also showed resonances in the vinyl region of the spectrum, indicating the presence of residual vinyl-sulfone groups bound in a pendant manner to the branched high MW polymer product. These pendant reactive vinyl-sulfone groups were observed as three well-defined multiplet signals at 6.4, 6.5 and 6.9 ppm. Note that the chemical structure of a pendant vinyl-sulfone group is illustrated in reaction SCHEME-A.

The inventors then demonstrated that the intensity of the vinyl-sulfone peaks were influenced by reaction conditions. A set of reactions was performed using the standard procedure described above. However, in this experiment the reactions were quenched with HCl at different times. After standard work-up, TFF purification and lyophilization, the branched high MW biopolymer products were analyzed by 1H-NMR. In the resulting set of spectra, the relative content of vinyl-sulfone functionality was determined by comparing the integrated area of the acetamide signal at 2.0-2.1 ppm (representing 3-hydrogen atoms) with the total integrated area of the three vinyl signals (also representing 3 hydrogen atoms). Because each chondroitin sulfate disaccharide repeat unit contains a single acetamide group, the ratio of integrated areas of these signals provides a measure of pendant vinyl-sulfone content on the branched high MW biopolymer. For example, if the intensities of the acetamide resonance and the vinyl resonances are the same (100:100), then every CS disaccharide repeat unit in the branched high MW biopolymer product would also contain one pendant vinyl sulfone group. The reaction conditions used in this set of experiments and the ratio of pendant vinyl-sulfone to acetamide integrated peak areas determined by 1H-NMR are set forth below.

| 1H-NMR Integration results | | | | | |
|---|---|---|---|---|---|
| Total CS (% wt) | DVS ratio | Stage1/Stage2 ratio | Reaction time (min) | 1H-NMR INTEGRAL | |
| | | | | Vinyl | Acetamide |
| 10 | 0.3 | 30/70 | 60 | 17.1 | 100.0 |
| | | | 90 | 8.4 | 100.0 |
| | | | 120 | 5.4 | 100.0 |
| 6 | 0.7 | 60/40 | 30 | 27.6 | 100.0 |
| | | | 60 | 19.3 | 100.0 |
| | | | 90 | 11.3 | 100.0 |
| | | | 120 | 7.7 | 100.0 |

The presence of residual vinyl-sulfone groups on the branched high MW biopolymer products from this process was not expected a priori. Initially it was anticipated that all reactive vinyl-sulfone would be consumed either by the hydroxyl groups on chondroitin sulfate as intended, or by hydroxide ions present in the highly alkaline (pH=13) reaction mixture. Indeed, the data shows that for a given set of reaction conditions, the relative intensity of the vinyl-sulfone signal diminishes as reaction time is increased. As the reaction time is extended, these pendant vinyl groups are consumed by available chondroitin sulfate from the Stage-2 addition to increase the MW of the product, or they are consumed by hydroxide ions to generate pendant hydroxyethyl sulfonyl moieties. Such pendant hydroxyethylsulfone groups have been reported as unreactive by-products in the preparation of biopolymer hydrogels using DVS as the crosslinking agent [Chang, G., Boney, J., Konowicz, P., Skrabut, E., Yu, L. P., Coury, A., & Jarrett, P. (2007, April). Assay development and application for the determination of percent modification of divinyl sulfone modified hyaluronan hydrogel. Poster. In Society for Biomaterials 2007 Annual Meeting. Chicago, IL.]. The ability of the inventive process to controllably provide branched high MW biopolymers bearing reactive vinyl sulfone groups was unexpected. Depending on conditions of the inventive process, the relative amount of reactive vinyl moieties on the resulting branched high MW biopolymers may be controlled to intentionally provide reactive biopolymer materials or alternatively provide biopolymer compositions with virtually no reactive functional groups. The inventors also propose that branched high MW GAG biopolymers bearing pendant reactive vinyl-sulfone groups are very useful. Such biopolymers are capable of effectively modifying surfaces or biosurfaces that contain reactive nucleophilic groups. For example, mammalian tissue surfaces are typically comprised of a variety of proteinaceous materials with both amine and sulfide groups from lysine and cysteine rich proteins. Such reactive groups on tissue and cell surfaces are well known to act as nucleophiles with appropriately reactive electrophilic agents including vinyl-sulfones. Vinyl-sulfone functional branched high MW biopolymers comprise a class of highly active surface-modifying biopolymers capable of durable surface modification on tissue and cell surfaces to provide useful treatment possibilities as medical devices and therapeutic materials. Branched high MW GAG biopolymers are uniquely innovative. These materials also have utility from their ability to produce a covalently bound coating of branched sulfated GAG biopolymer material onto an appropriately functionalized surface or biosurface such as a tissue surface.

Example 5: Preparation of an Amphiphilic, n-Hexyl-Functionalized, High MW Chondroitin Sulfate Composition with Bottlebrush Architecture in a 3-Stage, 1-Pot Process The inventors further demonstrated that the residual vinyl-sulfone groups pendant on a branched high MW GAG biopolymer can be effectively quenched with an appropriate nucleophile at the end of the synthetic process. Thus, a novel 3-stage process was designed and performed; stage-1 and stage-2 were performed as described in the previous examples to provide soluble high MW branched GAG biopolymer, however instead of quenching the reaction with the addition of acid, a nucleophilic quencher compound was added in excess, to fully react with all remaining vinyl-sulfone groups. After a short reaction time, the reaction was then neutralized with HCl, worked-up and purified as before. This novel 3-stage process produced a soluble, high MW, branched GAG biopolymer bearing the additional structural element or functional group derived from the quencher compound. Many structural elements or functional groups can be introduced into the polymer structure. This example illustrates the synthesis of a n-hexyl functionalized amphiphilic branched high MW GAG biopolymer prepared in a 3-stage process using n-hexylamine as the quencher agent in stage-3.

STAGE-1. Sodium chondroitin sulfate (0.500 g, 2.783 mmol equiv. hydroxyl groups) and sodium chloride (101 mg) were dissolved in 10.375 g DI water in a 20 mL reaction vessel. A clear colorless solution was obtained. DVS (0.329 g, 279 uL, 2.78 mmol) was added volumetrically with a microliter pipette. After gentle mixing, the solution was clear and colorless. Reaction was initiated by the addition of 1.153 mL of 1.0 N NaOH using a microliter pipette. With the addition of NaOH, the solution immediately became pale yellow in color and remained clear. The 11.5 ml reaction is 4.2 wt % in chondroitin sulfate and is 0.1 M in NaOH (pH 13). The reaction was gently mixed on a rotisserie.

STAGE-2. After 15 minutes, an additional portion of sodium chondroitin sulfate was added (0.500 g, 2.783 mmol equiv. hydroxyl groups), and the reaction mixture was agitated on a rotisserie. The reaction solution was 8 wt % in chondroitin sulfate and became slightly more viscous but remained clear and fluid.

STAGE-3. One hundred minutes after reaction initiation by introduction of NaOH, 25% of the reaction mixture was removed and quenched with HCl to provide a control material. To the remaining reaction mixture, n-hexylamine (0.282 ml, 2.09 mmol) was added and the clear reaction mixture was shaken and placed on a rotisserie mixer. The amount of amine quencher charged to the reaction was the same molar amount as the initial DVS charge. This amount was selected because it was thought to represent a large excess over the concentration of pendant vinyl-sulfone groups remaining on the growing polymer. After 30 minutes of mixing, the reaction was fully neutralized by adding 2.965 ml of 1.0N HCl using a microliter pipette. The pH of the solution was approximately 6.5. The clear fluid reaction mixture was diluted to 60 ml with PBS and was filtered through a 0.45-micron syringe filter.

PURIFICATION. A Spectrum Lab KR2i TFF system was used with a 250 ml feed reservoir and a 20-cm hollow fiber filter module containing modified polyethersulfone filter fibers (1 mm diameter, 100 kDa MWCO, 75 cm2 total surface area, part #D02-E100-10-N). The full 60 ml volume of the diluted product was loaded into the feed reservoir. The tangential flow filtration was initiated at 200 ml/min flow rate, with flow rate increasing to 300 ml/min keeping the inlet pressure below 25 psig. TFF was run in dialysis mode in which the volume of solution lost to permeate was continuously made up with additional PBS. In this way, the volume of retentate solution remained constant during the filtration procedure as five volumes (300 ml) of permeate was generated. The TFF was then continued in desalting mode by replenishing the feed reservoir with DI water (instead of PBS) and continuing filtration until an additional five volumes of permeate (300 ml) was obtained. The DI water replenishment was then suspended, and the filtration was run in concentration mode to reduce the retentate volume down to approximately 40 mL. The TFF was then stopped and the system was flushed (10 ml DI water) to recover hold-up volume. The purified retentate was then dried by lyophilization for 72 hours, yielding purified product (0.468 g) as a white fluffy solid.

Analysis of the product by Wyatt DynaPro Nanostar DLS showed a hydrodynamic radius of 25 nm and a Mw estimate from static light scattering was 203 kDa. Analysis of the product by proton NMR showed total absence of vinyl resonances, and several new peaks representing the n-hexyl group. The ratio of integrated peak areas between the chondroitin sulfate acetamide peak and the methyl peak of the hexyl group was 100:17 suggesting that the product contains n-hexyl substituent on 17% of the chondroitin sulfate disaccharide units. The amphiphilic nature of the product was evident by the appearance of low surface tension of dilute aqueous solutions (some foam formation on shaking).

Example 6: Preparation of an Amphiphilic, n-Octyl-Functionalized, High MW Chondroitin Sulfate Composition with Bottlebrush Architecture in a 3-Stage, 1-Pot Process The procedure described for Example-5 was repeated exactly as described above, except that in STAGE-3, n-octylamine (0.345 ml, 2.09 mmol) was added as the quencher. Unlike Example-20, the addition of n-octylamine caused the reaction mixture to become thick and cloudy. An additional volume (12 ml) of deionized water was therefore added to the stage-3 reaction to restore clarity and flow. This solution was then worked-up and purified as described in Example 20 yielding purified product (0.512 g) as a white fluffy solid. Analysis of the product by Wyatt DynaPro Nanostar DLS showed a hydrodynamic radius of 36 nm and a Mw estimate from static light scattering was 320 kDa. Analysis of the product by proton NMR showed total absence of vinyl resonances, and several new peaks representing the n-hexyl group. The ratio of integrated peak areas between the chondroitin sulfate acetamide peak and the methyl peak of the hexyl group was 100:12 suggesting that the product contains n-hexyl substituent on 13% of the chondroitin sulfate disaccharide units. The amphiphilic nature of the product was evident by the appearance of low surface tension of dilute aqueous solutions (strong foam formation on shaking).

Example 7: Preparation of a Pyrrolidine-Functionalized, High MW Chondroitin Sulfate Composition with Bottlebrush Architecture in a 3-Stage, 1-Pot Process The 3-stage procedure described for Example-5 was repeated exactly as described above, except that in STAGE-3, pyrrolidine (0.174 ml, 2.09 mmol) was added as the quencher. The reaction mixture remained clear and flowable after the addition of pyrrolidine. This solution was then worked-up and purified as described in Example 20 yielding purified product (0.373 g) as a white fluffy solid. Analysis of the product by Wyatt DynaPro Nanostar DLS showed a hydrodynamic radius of 27 nm and a Mw estimate from static light scattering was 253 kDa. Analysis of the product by proton NMR showed the total absence of vinyl resonances. In this case the methylene resonances of the added pyrrolidine group were obscured by the chondroitin sulfate peaks.

Example 8: Preparation of a Glutathione-Functionalized, High MW Chondroitin Sulfate Composition with Bottlebrush Architecture in a 3-Stage, 1-Pot Process The 3-stage procedure described for Example-5 was repeated as described above, except that in STAGE-3, glutathione (0.642 g, 2.09 mmol) was added as the quencher. The solid glutathione dissolved very quickly in the reaction mixture to give a clear solution. As was seen in Example-20, the reaction mixture remained clear and flowable after the addition of glutathione. This solution was then worked-up and purified, yielding purified product (0.369 g) as a white fluffy solid. Analysis of the product by Wyatt DynaPro Nanostar DLS showed a hydrodynamic radius of 21 nm and a Mw estimate from static light scattering was 143 kDa. Analysis of the product by proton NMR showed the total absence of vinyl resonances. In this case, the resonances of the added glutathione group were partly obscured by the chondroitin sulfate peaks.

Example 9: Preparation of a Lactosylamine-Functionalized, High MW Chondroitin Sulfate Composition with Bottlebrush Architecture in a 3-Stage, 1-Pot Process The 3-stage procedure described for Example-5 was repeated (on a scale of 0.500 g of sodium chondroitin sulfate), except that in STAGE-3, lactosylamine was added as the quencher. The reaction mixture remained clear and flowable after the addition of lactosylamine. This solution was then worked-up and purified yielding purified product (0.373 g) as a white fluffy solid. Analysis of the product by Wyatt DynaPro Nanostar DLS showed a hydrodynamic radius of 27 nm and a Mw estimate from static light scattering was 253 kDa. Analysis of the product by proton NMR shows the total absence of vinyl resonances. In this case the methylene resonances of the added lactosyl group are obscured by the chondroitin sulfate peaks.

Example 10: Preparation of a 2-Ethoxyethylamine-Functionalized, High MW Chondroitin Sulfate Composition with Bottlebrush Architecture in a 3-Stage, 1-Pot Process STAGE-1. Sodium chondroitin sulfate (0.1730 g, 2.783 mmol equiv. hydroxyl groups) and sodium chloride (0.0465 mg) were dissolved in 4.7790 g DI water in a 20 mL reaction vessel. A clear colorless solution was obtained. DVS (0.091 g, 77.1 µL, 0.786 mmol) was added volumetrically with a microliter pipette. After gentle mixing, the solution was clear and colorless. Reaction was initiated by the addition of 0.531 mL of 1.0 N NaOH using a microliter pipette. With the addition of NaOH, the solution immediately became pale yellow in color and remained clear. The reaction is 3.2 wt % in chondroitin sulfate and is 0.1 M in NaOH (pH 13). The reaction was gently mixed on a rotisserie.

STAGE-2. After 15 minutes, an additional portion of sodium chondroitin sulfate was added (0.5180 g, 2.783 mmol equiv. hydroxyl groups), and the reaction mixture was agitated on a rotisserie. The reaction solution was 11.5 wt % in chondroitin sulfate and became slightly more viscous but remained clear and fluid.

STAGE-3. One hundred twenty minutes after reaction initiation by introduction of NaOH, the reaction solution was diluted using 2 mL DI water. After gentle mixing, the solution remained clear and colorless. The reaction solution was 8.1 wt % in chondroitin sulfate and became less viscous. After 30 minutes, 0.0805 mL 2-exothyethylamine was added to the reaction solution. The amount of amine quencher charged to the reaction was the same molar amount as the initial DVS charge. This amount was selected because it was thought to represent a large excess over the concentration of pendant vinyl-sulfone groups remaining on the growing polymer. After 15 minutes of mixing, the reaction was fully neutralized by adding 0.981 mL of 1.0N HCl using a microliter pipette. The pH of the solution was approximately 6.5. The clear fluid reaction mixture was diluted to 40 mL with PBS and was filtered through a 0.45-micron syringe filter.

PURIFICATION. A Spectrum Lab KR2i TFF system was used with a 50 mL feed fibers (0.5 mm diameter, 100 kDa MWCO, 115 cm² total surface area, part #D02-E100-05-N). The full 40 mL volume of the diluted product was loaded into the feed reservoir. The tangential flow filtration was initiated at 150 ml/min flow rate, and the transmembrane pressure was set to increasing to 18 keeping the inlet pressure below 25 psig. TFF was run in an automated dialysis mode in which the volume of solution lost to permeate was continuously made up with additional PBS. In this way, the volume of retentate solution remained constant during the filtration procedure as five volumes (200 mL) of permeate was generated. The TFF was then continued in desalting mode by replenishing the feed reservoir with DI water (instead of PBS) and continuing filtration until an additional five volumes of permeate (200 mL) was obtained. The DI water replenishment was then suspended, and the filtration was run in concentration mode to reduce the retentate volume back down to approximately 40 mL. The TFF was then stopped, and the system was flushed (5 mL DI water) to recover hold-up volume. The purified retentate was filtered through a 0.2-micron syringe filter and then dried by lyophilization for 72 hours, yielding purified product (0.3567 g) as a white fluffy solid.

Analysis of the product by Wyatt DynaPro Nanostar DLS showed a hydrodynamic radius of 43.5 nm and a Mw estimate from static light scattering was 1902 kDa. Analysis of the product by SEC-MALLS indicated an Mn=268000 and Mw=2470000. Analysis of the product by proton NMR showed total absence of vinyl resonances, and several new peaks representing the methyl group of the 2-ethoxyethylamine. The ratio of integrated peak areas between the chondroitin sulfate acetamide peak and the methyl peak of the 2-ethoxyethylamine group was 100:4 suggesting that the product contains 2-ethoxyethylamine substituent on 4% of the chondroitin sulfate disaccharide units.

| Example | Functional Unit Appended | DLS Radius (nm) | DLS (Mw, kDa) | SEC-MALLS (Mn, Kda) | SEC-MALLS (Mw, Kda) | $^1$H NMR Peak | $^1$H NMR Ratio |
|---|---|---|---|---|---|---|---|
| 11 | Piperidine | 32.1 | 1105 | — | — | Vinyl signal not detected | |
| 12 | 2-(Methoxyethoxy) ethanamine | 19.5 | 442 | — | — | Vinyl signal not detected | |
| 13 | 4-Methylpiperidine-4-ol | 20.6 | 488 | — | — | Vinyl signal not detected | |
| 14 | 4-Methylpiperidine | 39.4 | 1632 | — | — | Vinyl signal not detected | |
| 15 | 3-Aminooxetane | 43.4 | 1900 | — | — | Vinyl signal not detected | |
| 16 | N-(2-Aminoethyl) biotinamide | 31.8 | 1090 | 176 | 971 | Biotin methine | 3.7% |
| 17 | Biotin-PEG7-amine | 46.8 | 2102 | 300 | 2120 | Biotin methine | 4% |

Example 18: Preparation of a High Vinyl-Functionalized (1 of 4), High MW Chondroitin Sulfate Composition with Bottlebrush Architecture in a 3-Stage, 1-Pot Process The inventors demonstrated that the additional vinyl-sulfone groups can be added to the branched high MW GAG biopolymer while retaining solubility. In stage 3, a key dilution step is performed, permitting reaction with additional crosslinking agent in stage 4.

STAGE-1 and STAGE-2 of this example were run with identical conditions to Example 10.

STAGE-3. One hundred twenty minutes after reaction initiation by introduction of NaOH, the reaction solution was diluted using 2 mL DI water. After gentle mixing, the solution remained clear and colorless. The reaction solution was 8.1 wt % in chondroitin sulfate and became less viscous. After 5 minutes, 0.0771 mL DVS was added to the reaction solution. The amount of DVS added to the reaction was the same molar amount as the initial DVS charge. After 15 minutes of mixing, the reaction was fully neutralized by adding 0.531 mL of 1.0N HCl using a microliter pipette. The pH of the solution was approximately 6.5. The clear fluid reaction mixture was diluted to 40 mL with PBS and was filtered through a 0.45-micron syringe filter.

PURIFICATION. A Spectrum Lab KR2i TFF system was used with a 50 mL feed fibers (0.5 mm diameter, 100 kDa MWCO, 115 cm$^2$ total surface area, part #D02-E100-05-N). The full 40 mL volume of the diluted product was loaded into the feed reservoir. The tangential flow filtration was initiated at 150 ml/min flow rate, and the transmembrane pressure was set to increasing to 18 keeping the inlet pressure below 25 psig. TFF was run in an automated dialysis mode in which the volume of solution lost to permeate was continuously made up with additional PBS. In this way, the volume of retentate solution remained constant during the filtration procedure as five volumes (200 mL) of permeate was generated. The TFF was then continued in desalting mode by replenishing the feed reservoir with DI water (instead of PBS) and continuing filtration until an additional five volumes of permeate (200 mL) was obtained. The DI water replenishment was then suspended, and the filtration was run in concentration mode to reduce the retentate volume back down to approximately 40 mL. The TFF was then stopped, and the system was flushed (5 mL DI water) to recover hold-up volume. The purified retentate was filtered through a 0.2-micron syringe filter and then dried by lyophilization for 72 hours, yielding purified product (0.3772 g) as a white fluffy solid.

Analysis of the product by Wyatt DynaPro Nanostar DLS showed a hydrodynamic radius of 44 nm and a Mw estimate from static light scattering was 393 kDa. Analysis of the product by SEC-MALLS indicated an Mn=167000 and Mw=677000. Analysis of the product by proton NMR showed a higher value vinyl resonance signal. The ratio of integrated peak areas between the chondroitin sulfate acetamide peak and the vinyl peak was 100:24 suggesting that the product contains vinyl on 24% of the chondroitin sulfate disaccharide units.

Example 19: Preparation of a Mid High Vinyl-Functionalized (2 of 4), High MW Chondroitin Sulfate Composition with Bottlebrush Architecture in a 3-Stage, 1-Pot Process STAGE-1 and STAGE-2 of this example were run with identical conditions to Example 10 except a stir plate was used as mixing method instead of rotisserie stirring.

STAGE-3. One hundred five minutes after reaction initiation by introduction of NaOH, the reaction solution was diluted using 4 mL DI water. After gentle mixing, the solution remained clear and colorless. The reaction solution was 6.3 wt % in chondroitin sulfate and became slightly less viscous. After 15 minutes, 0.0578 mL DVS was added to the reaction solution. The amount of DVS added to the reaction was equal to 75% of the initial DVS charge. After 15 minutes of mixing, the reaction was fully neutralized by adding 0.581 mL of 1.0N HCl using a microliter pipette. The pH of the solution was approximately 6.5. The clear fluid reaction mixture was diluted to 40 mL with PBS and was filtered through a 0.45-micron syringe filter.

PURIFICATION. A Spectrum Lab KR2i TFF system was used with a 50 mL feed reservoir and a 20-cm hollow fiber filter module containing modified polyethersulfone filter fibers (0.5 mm diameter, 100 kDa MWCO, 115 cm$^2$ total surface area, part #D02-E100-05-N). The full 40 mL volume of the diluted product was loaded into the feed reservoir. The tangential flow filtration was initiated at 150 ml/min flow rate, and the transmembrane pressure was set to increasing to 18 keeping the inlet pressure below 25 psig. TFF was run in an automated dialysis mode in which the volume of solution lost to permeate was continuously made up with additional PBS. In this way, the volume of retentate solution remained constant during the filtration procedure as five volumes (200 mL) of permeate was generated. The TFF was then continued in desalting mode by replenishing the feed reservoir with DI water (instead of PBS) and continuing filtration until an additional five volumes of permeate (200 mL) was obtained. The DI water replenishment was then suspended, and the filtration was run in concentration mode to reduce the retentate volume back down to approximately 40 mL. The TFF was then stopped, and the system was flushed (5 mL DI water) to recover hold-up volume. The purified retentate was filtered through a 0.2-micron syringe filter and then dried by lyophilization for 72 hours, yielding purified product (0.3800 g) as a white fluffy solid.

Analysis of the product by Wyatt DynaPro Nanostar DLS showed a hydrodynamic radius of 46.4 nm and a Mw estimate from static light scattering was 375 kDa. Analysis of the product by proton NMR showed a higher valued vinyl resonance signal. The ratio of integrated peak areas between the chondroitin sulfate acetamide peak and the vinyl peaks was 100:16 suggesting that the product contains residual vinyl on 16% of the chondroitin sulfate disaccharide units.

Example 20: Preparation of a Medium Vinyl-Functionalized (3 of 4), High MW Chondroitin Sulfate Composition with Bottlebrush Architecture in a 3-Stage, 1-Pot Process STAGE-1 and STAGE-2 of this example were run with identical conditions to Example except a stir plate was used as mixing method instead of rotisserie stirring.

STAGE-3. One hundred five minutes after reaction initiation by introduction of NaOH, the reaction solution was diluted using 4 mL DI water. After gentle mixing, the solution remained clear and colorless. The reaction solution was 6.3 wt % in chondroitin sulfate and became less viscous. After 15 minutes, 0.0386 mL DVS was added to the reaction solution. The amount of DVS added to the reaction was equal to 50% of the initial DVS charge. After 15 minutes of mixing, the reaction was fully neutralized by adding 0.581 mL of 1.0N HCl using a microliter pipette. The pH of the solution was approximately 6.5. The clear fluid reaction mixture was diluted to 40 mL with PBS and was filtered through a 0.45-micron syringe filter.

PURIFICATION. A Spectrum Lab KR2i TFF system was used with a 50 mL feed reservoir and a 20-cm hollow fiber filter module containing modified polyethersulfone filter fibers (0.5 mm diameter, 100 kDa MWCO, 115 cm$^2$ total surface area, part #D02-E100-05-N). The full 40 mL volume of the diluted product was loaded into the feed reservoir. The tangential flow filtration was initiated at 150 ml/min flow rate, and the transmembrane pressure was set to increasing to 18 keeping the inlet pressure below 25 psig. TFF was run in an automated dialysis mode in which the volume of solution lost to permeate was continuously made up with additional PBS. In this way, the volume of retentate solution remained constant during the filtration procedure as five volumes (200 mL) of permeate was generated. The TFF was then continued in desalting mode by replenishing the feed reservoir with DI water (instead of PBS) and continuing filtration until an additional five volumes of permeate (200 mL) was obtained. The DI water replenishment was then suspended, and the filtration was run in concentration mode to reduce the retentate volume back down to approximately 40 mL. The TFF was then stopped, and the system was flushed (5 mL DI water) to recover hold-up volume. The purified retentate was filtered through a 0.2-micron syringe filter and then dried by lyophilization for 72 hours, yielding purified product (0.3350 g) as a white fluffy solid.

Analysis of the product by Wyatt DynaPro Nanostar DLS showed a hydrodynamic radius of 38.1 nm and a Mw estimate from static light scattering was 340 kDa. Analysis of the product by proton NMR showed a higher valued vinyl resonance signal. The ratio of integrated peak areas between the chondroitin sulfate acetamide peak and the vinyl peaks was 100:12 suggesting that the product contains residual vinyl on 12% of the chondroitin sulfate disaccharide units.

Example 21: Preparation of a Lower Vinyl-Functionalized (3 of 3), High MW Chondroitin Sulfate Composition with Bottlebrush Architecture in a 3-Stage, 1-Pot Process STAGE-1 and STAGE-2 of this example were run with identical conditions to Example except a stir plate was used as the mixing method instead of rotisserie stirring.

STAGE-3. One hundred five minutes after reaction initiation by introduction of NaOH, the reaction solution was diluted using 4 mL DI water. After gentle mixing, the solution remained clear and colorless. The reaction solution was 6.3 wt % in chondroitin sulfate and became less viscous. After 45 minutes, 0.0193 mL DVS was added to the reaction solution. The amount of DVS added to the reaction was equal to 25% of the initial DVS charge. After 15 minutes of mixing, the reaction was fully neutralized by adding 0.581 mL of 1.0N HCl using a microliter pipette. The pH of the solution was approximately 6.5. The clear fluid reaction mixture was diluted to 40 mL with PBS and was filtered through a 0.45-micron syringe filter.

PURIFICATION. A Spectrum Lab KR2i TFF system was used with a 50 mL feed reservoir and a 20-cm hollow fiber filter module containing modified polyethersulfone filter fibers (0.5 mm diameter, 100 kDa MWCO, 115 cm$^2$ total surface area, part #D02-E100-05-N). The full 40 mL volume of the diluted product was loaded into the feed reservoir. The tangential flow filtration was initiated at 150 ml/min flow rate, and the transmembrane pressure was set to increasing to 18 keeping the inlet pressure below 25 psig. TFF was run in an automated dialysis mode in which the volume of solution lost to permeate was continuously made up with additional PBS. In this way, the volume of retentate solution remained constant during the filtration procedure as five volumes (200 mL) of permeate was generated. The TFF was then continued in desalting mode by replenishing the feed reservoir with DI water (instead of PBS) and continuing filtration until an additional five volumes of permeate (200 mL) was obtained. The DI water replenishment was then suspended, and the filtration was run in concentration mode to reduce the retentate volume back down to approximately 40 mL. The TFF was then stopped, and the system was flushed (5 mL DI water) to recover hold-up volume. The purified retentate was filtered through a 0.2-micron syringe filter and then dried by lyophilization for 72 hours, yielding purified product (0.2818 g) as a white fluffy solid.

Analysis of the product by Wyatt DynaPro Nanostar DLS showed a hydrodynamic radius of 28.25 nm and a Mw estimate from static light scattering was 217 kDa. Analysis of the product by proton NMR showed a higher valued vinyl resonance signal. The ratio of integrated peak areas between the chondroitin sulfate acetamide peak and the vinyl peaks was 100:8 suggesting that the product contains residual vinyl on 8% of the chondroitin sulfate disaccharide units.

Example 22: Preparation of an Amphiphilic, n-Hexyl-Functionalized, High MW Chondroitin Sulfate Composition with Bottlebrush Architecture in a 4-Stage, 1-Pot Process The inventors further demonstrated that the highly substituted vinyl-sulfone branched high MW GAG biopolymer can be effectively quenched n-hexyl amine to produce a highly substituted ambiphilic polymer.

STAGE-1 and STAGE-2 of this example were run with identical conditions to Example except a stir plate was used as mixing method instead of rotisserie stirring.

STAGE-3. One hundred five minutes after reaction initiation by introduction of NaOH, the reaction solution was diluted using 4 mL DI water. After gentle mixing, the solution remained clear and colorless. The reaction solution was 6.3 wt % in chondroitin sulfate and became less viscous. After 15 minutes, 0.0578 mL DVS was added to the reaction solution. The amount of DVS added to the reaction was equal to 75% of the initial DVS charge.

STAGE-4. After 15 minutes of mixing, 0.1009 mL hexylamine was added to the reaction solution. The amount of amine quencher charged to the reaction was the same molar amount as the initial DVS charge. This amount was selected because it was thought to represent a large excess over the concentration of pendant vinyl-sulfone groups remaining on the growing polymer. The solution immediately became cloudy upon the addition of the hexylamine. After minutes of mixing, the reaction was fully neutralized by adding 1.181 mL of 1.0N HCl using a microliter pipette. The pH of the solution was approximately 6.5. The clear fluid reaction mixture was diluted to 40 mL with PBS and was filtered through a 0.45-micron syringe filter.

PURIFICATION. A Spectrum Lab KR2i TFF system was used with a 50 mL feed reservoir and a 20-cm hollow fiber filter module containing modified polyethersulfone filter fibers (0.5 mm diameter, 100 kDa MWCO, 115 cm$^2$ total surface area, part #D02-E100-05-N). The full 40 mL volume of the diluted product was loaded into the feed reservoir. The tangential flow filtration was initiated at 150 mL/min flow rate, and the transmembrane pressure was set to increasing to 18 keeping the inlet pressure below 25 psig. TFF was run in an automated dialysis mode in which the volume of solution lost to permeate was continuously made up with additional PBS. In this way, the volume of retentate solution remained constant during the filtration procedure as five volumes (200 mL) of permeate was generated. The TFF was then continued in desalting mode by replenishing the feed reservoir with DI water (instead of PBS) and continuing filtration until an additional five volumes of permeate (200 mL) was obtained. The DI water replenishment was then suspended, and the filtration was run in concentration mode to reduce the retentate volume back down to approximately 40 mL. The TFF was then stopped, and the system was flushed (5 mL DI water) to recover hold-up volume. The purified retentate was filtered through a 0.2-micron syringe filter and then dried by lyophilization for 72 hours, yielding purified product (0.4102 g) as a white fluffy solid.

Analysis of the product by Wyatt DynaPro Nanostar DLS showed a hydrodynamic radius of 34.5 nm and a Mw estimate from static light scattering was 284 kDa. Analysis of the product by proton NMR showed total absence of vinyl resonances, and several new peaks representing the n-hexyl group. The ratio of integrated peak areas between the chondroitin sulfate acetamide peak and the methyl peak of the hexyl group was 100:18 suggesting that the product contains n-hexyl substituent on 18% of the chondroitin sulfate disaccharide units. The amphiphilic nature of the product was evident by the appearance of low surface tension of dilute aqueous solutions (some foam formation on shaking).

Example 23: Preparation of a Boronic Acid and 2-Ethoxyethylamine-Functionalized, High MW Chondroitin Sulfate Composition with Bottlebrush Architecture in a 5-Stage, 1-Pot Process The inventors further demonstrated that the residual vinyl-sulfone groups pendant on a branched high MW GAG biopolymer can be effectively quenched with an appropriate nucleophile at the end of the synthetic process. Thus, a novel 6-stage process was designed and performed; stage-1 and stage-2 were performed as described in the previous examples to provide soluble high MW branched GAG biopolymer, however instead of quenching the reaction with the addition of acid, the solution was diluted with DI water in stage 3 and had additional DVS added in stage 4. In stage 5, a nucleophilic quencher compound was added in excess, to react with some of the remaining vinyl-sulfone groups. This specific nucleophile was found to not quench all the residual vinyl signals therefore, in stage 6 an additional nucleophilic quencher was added to ensure the vinyl signals were fully quenched. After a short reaction time, the reaction was then neutralized with HCl, worked-up and purified as before. This novel 6-stage process produced a soluble, high MW, branched GAG biopolymer bearing the additional structural element or functional group derived from the quencher compound. Many structural elements or functional groups can be introduced into the polymer structure. This example illustrates the synthesis of a n-hexyl functionalized amphiphilic branched high MW GAG biopolymer prepared in a 6-stage process using DI water in stage 3, DVS in stage 4, n-hexylamine as the quencher agent in stage-5, and 2-ethoxyethylamine in stage-6.

STAGE-1 and STAGE-2 of this example were run with identical conditions to Example except a stir plate was used as mixing method instead of rotisserie stirring.

STAGE-3. One hundred five minutes after reaction initiation by introduction of NaOH, the reaction solution was diluted using 4 mL DI water. After gentle mixing, the solution remained clear and colorless. The reaction solution was 6.3 wt % in chondroitin sulfate and became slightly less viscous. After 15 minutes, 0.0193 mL DVS was added to the reaction solution. The amount of DVS added to the reaction was equal to 25% of the initial DVS charge.

STAGE-4. After 15 minutes, 0.2017 g heterocyclic Compound ((4-((2-aminoethyl)carbamoyl)-3-fluorophenyl)boronic acid hydrochloride, $C9H_{13}BClFN_2O_3$) produced by Jiangyin PharmaAdvance, Inc. was added to the reaction solution. Upon this addition the pH of the reaction solution decreased therefore HCl was added until pH=13. With gentle mixing the solution became slightly cloudy. After 15 minutes, 0.0805 mL 2-exothyethylamine was added to the reaction solution. The amount of amine quencher charged to the reaction was the same molar amount as the initial DVS charge. This amount was selected because it was thought to represent a large excess over the concentration of pendant vinyl-sulfone groups remaining on the growing polymer. After 15 minutes of mixing, the reaction was fully neutralized by adding 0.981 mL of 1.0N HCl using a microliter pipette. The pH of the solution was approximately 6.5. The clear fluid reaction mixture was diluted to 40 mL with PBS and was filtered through a 0.45-micron syringe filter.

PURIFICATION. A Spectrum Lab KR2i TFF system was used with a 50 mL feed reservoir and a 20-cm hollow fiber filter module containing modified polyethersulfone filter fibers (0.5 mm diameter, 100 kDa MWCO, 115 cm$^2$ total surface area, part #D02-E100-05-N). The full 40 mL volume of the diluted product was loaded into the feed reservoir. The tangential flow filtration was initiated at 150 mL/min flow rate, and the transmembrane pressure was set to increasing to 18 keeping the inlet pressure below 25 psig. TFF was run in an automated dialysis mode in which the volume of solution lost to permeate was continuously made up with additional PBS. In this way, the volume of retentate solution remained constant during the filtration procedure as five volumes (200 mL) of permeate was generated. The TFF was then continued in desalting mode by replenishing the feed reservoir with DI water (instead of PBS) and continuing filtration until an additional five volumes of permeate (200 mL) was obtained. The DI water replenishment was then suspended, and the filtration was run in concentration mode to reduce the retentate volume back down to approximately 40 mL. The TFF was then stopped, and the system was flushed (5 mL DI water) to recover hold-up volume. The purified retentate was filtered through a 0.2-micron syringe filter and then dried by lyophilization for 72 hours, yielding purified product (0.3846 g) as a white fluffy solid.

Analysis of the product by Wyatt DynaPro Nanostar DLS showed a hydrodynamic radius of 25.1 nm and a Mw estimate from static light scattering was 701.4 kDa. Analysis of the product by proton NMR shows the total absence of vinyl resonances, and the expected aryl and 2-ethoxyethylamine resonances. The ratio of integrated peak areas between the chondroitin sulfate acetamide peak and the aryl and 2-ethoxyethylamine peak were 100:6.9 and 100:1.5, respectively, suggesting that the product contains aryl and 2-ethoxyethylamine substituent on 6.9% and 1.5% of the chondroitin sulfate disaccharide units.

Example 24: Preparation of a Lactosylamine-Functionalized, High MW Chondroitin Sulfate Composition with Bottlebrush Architecture in a 2-Stage, 1-Pot Process The inventors further demonstrated that the residual vinyl-sulfone groups pendant on a branched high MW GAG biopolymer can be effectively quenched with an appropriate nucleophile at the end of the synthetic process. Thus, a novel 2-stage process was designed and performed; a high vinyl SuperGAG and lactosylamine were dissolved in saline at pH 13 to quench residual vinyl groups with lactosylamine. Lactosylamine has been observed to not quenched all the residual vinyl groups so an additional nucleophile was added in stage-2 to ensure all residual vinyl signals were quenched. After a short reaction time, the reaction was then neutralized with HCl, worked-up and purified as before. This novel 2-stage process produced a soluble, high MW, branched GAG biopolymer bearing the additional structural element or functional group derived from the quencher compound. Many structural elements or functional groups can be introduced into the polymer structure. This example illustrates the synthesis of a lactosylamine and 2-ethoxyethylamine functionalized branched high MW GAG biopolymer prepared in a 2-stage process using lactosylamine as the quencher agent in stage-1 and 2-ethoxyethylamine in stage-2.

STAGE-1. SuperGAG 007-033-2 (0.100 g) and lactosylamine (0.500 mg) were dissolved in 3.0 g 0.9% saline in a 20 mL reaction vessel. A clear colorless solution was obtained. Reaction was initiated by the addition of 0.600 mL of 1.0 N NaOH using a microliter pipette. With the addition of NaOH, the solution remained clear and colorless. The reaction was gently mixed on a stir plate with a stir bar.

STAGE-2. After 45 minutes, 0.0805 mL 2-ethoxyethylamine was added to the reaction vial. The amount of amine quencher charged to the reaction was the same molar amount as the initial DVS charge in the SuperGAG synthesis process described above. This amount was selected because it was thought to represent a large excess over the concentration of pendant vinyl-sulfone groups remaining on the growing polymer. After gentle mixing, the solution remained clear and colorless. After 15 minutes of mixing, the reaction was fully neutralized by adding 0.981 mL of 1.0N HCl using a microliter pipette. The pH of the solution was approximately 6.5. The clear fluid reaction mixture was diluted to 40 mL with PBS and was filtered through a 0.45-micron syringe filter.

PURIFICATION. A Spectrum Lab KR2i TFF system was used with a 50 mL feed reservoir and a 20-cm hollow fiber filter module containing modified polyethersulfone filter fibers (0.5 mm diameter, 100 kDa MWCO, 115 cm² total surface area, part #D02-E100-05-N). The full 40 mL volume of the diluted product was loaded into the feed reservoir. The tangential flow filtration was initiated at 150 mL/min flow rate, and the transmembrane pressure was set to 15, increasing to 18 keeping the inlet pressure below 25 psig. TFF was run in an automated dialysis mode in which the volume of solution lost to permeate was continuously made up with additional PBS. In this way, the volume of retentate solution remained constant during the filtration procedure as five volumes (200 mL) of permeate was generated. The TFF was then continued in desalting mode by replenishing the feed reservoir with DI water (instead of PBS) and continuing filtration until an additional five volumes of permeate (200 mL) was obtained. The DI water replenishment was then suspended, and the filtration was run in concentration mode to reduce the retentate volume back down to approximately 40 mL. The TFF was then stopped, and the system was flushed (5 mL DI water) to recover hold-up volume. The purified retentate was filtered through a 0.2-micron syringe filter and then dried by lyophilization for 72 hours, yielding purified product (0.0.069 g) as a white fluffy solid.

Analysis of the product by Wyatt DynaPro Nanostar DLS showed a hydrodynamic radius of 48.3 nm and a Mw estimate from static light scattering was 2307 kDa. Analysis of the product by proton NMR showed total absence of vinyl resonances, and several new peaks representing the methyl group in 2-ethoxyethylamine. In this example the resonances of the added lactosylamine groups are obscured by the chondroitin sulfate peaks; quantitation is not possible but inspection reveals that the spectrum has changed in a manner consistent with addition of the lactosylamine. The ratio of integrated peak areas between the chondroitin sulfate acetamide peak and the methyl peak was 100:12 suggesting that the product contains 2-ethoxyethylamine substituent on 12% of the chondroitin sulfate disaccharide units.

Example 25: Evaluation of Compositions for Treatment of Interstitial Cystitis Coupled with MRI Quantified Bladder Permeability in the Rat A rat model is used to replicate the leaky bladder pathology that is understood to be a major contributor in the development of interstitial cystitis (IC). Female ovariectomized (OVX) Sprague-Dawley rats (250-300 g) are purchased from Charles River Laboratories. Rats are housed two per cage under controlled temperature and humidity. OVX rats are used to avoid any effects of hormonal cycling, and because male rats cannot be catheterized through the urethra. All animals have free access to food and water and are acclimated to the facility housing for a minimum of 1 week before experimentation. The experimental protocol is approved by the relevant Institutional Animal Care and Use Committee.

Transurethral Treatment

OVX female SAS Sprague Dawley® rats at age 7-weeks weighing 250 to 300 grams are treated with protamine sulfate (PS) to induce leaky bladder as described in the literature [Towner, et. al., Journal of Urology 2015, vol 193, pp 1394-1400]. Rats are anesthetized with isoflurane (3%) with a steady supply of oxygen for a period of approximately 10 min, and the bladder is emptied following catheterization using a lubricated 18-gauge intravenous catheter (Surflo, Terumo, Elkton, MD) and a custom-made guide wire. Care is taken not to traumatize the bladder by stopping the catheter just after it passes by the pubic bones and not allowing it to "bottom out." Animals are monitored for hematuria as an indicator of bladder trauma, and any animals with blood in the urine or solutions are not used. PS (1 mg/ml in 40011.1 saline) is slowly instilled into the bladder through the catheter. After 15 min, the bladder is emptied by applying lower abdominal pressure. The bladders are then rinsed with saline (40011.1×3), after which the transurethral catheter is removed and animals are returned to their home cages.

MRI Imaging of Bladder and Colon

Bladder permeability is assessed by Magnetic Resonance Imaging (MRI). Rats are anesthetized with isoflurane (1.5% to 3.0%) with 800 to 1,000 ml 02 for MRI experiments. MM is performed on a 7-Tesla 30 cm bore BioSpec® MM system. For bladder images, in vivo diagnostic CE-MRI specifically uses Gd-DTPA (0.2 mmol Gd/kg diluted to 800 ml in saline) administered via an intravesical catheter to visualize bladder urothelium loss of permeability on bladder contrast images. Bladder contrast images are obtained every 3 minutes 43 seconds for a total of 20 minutes. For colon contrast images, Gd-DTPA (0.2 mmol Gd/kg diluted to 200 ml in saline) is administered intravenously via a 24 gauge 0.75-inch BD INSYTE™ AUTOGUARD™ shielded intravenous tail vein catheter. Images are obtained for 30 minutes. All MRI images are acquired using a T1-weighted RARE (rapid acquisition with relaxation enhancement) MM pulse sequence with certain parameters, including repetition time 1,200 milliseconds, echo time 9 milliseconds, a RARE factor of 4, 4 averages, 1 mm image slice thickness, 256×256 matrix and 6.5×6.5 cm2 field of view with motion and fat suppression.

Biopolymer Treatment

The inventive biopolymers are instilled into the leaky bladder 24 hours after PS treatment. The biopolymers are administered via transurethral catheterization 24 hrs. after PS exposure. The biopolymers are dissolved in saline (20 mg/ml) and sterile filtered (0.2 μm PVDF syringe filter) prior to administration. Biopolymer administration is performed under the anesthesia protocol described for the MM imaging.

MRI is performed 24 hours after PS exposure, immediately after polymer treatment. MRI is performed again 5-days following PS exposure, 4-days after biopolymer treatment.

Data Analysis and Statistics

MRI signal intensity is measured from regions of interest (ROIs) in images. Four or 5 ROIs can be used in high intensity regions in the bladder periphery, colon mucosa, adipose body surrounding the bladder, surrounding colon tissues and medial thigh muscle along with corresponding regions in control data sets. These data can be displayed using ParaVision™ version 5.0. Statistical analysis is done using ANOVA with the post Tukey multiple comparison test to evaluate differences in treatment groups using InStat (GRAPH-PAD®). Signal intensity differences between groups with $p<0.05$, $<0.01$ or $<0.001$ is considered statistically significant.

Example 26: Evaluation of Compositions for Treatment of Interstitial Cystitis

Two animal models were used. A rat model described in detail previously was used to confirm that the SuperGAG restores impermeability using the TEER "gold standard." This same model was used to confirm that restoring bladder impermeability abrogates the abdominal pain result. The restoration of impermeability also was confirmed in a transgenic mouse model that is receiving increasing acceptance as a model for IC/BPS using MRI as developed in our labs. The mouse bladder is too small for reliable TEER measurements.

Beginning at 9 a.m. (Day 0) OVX female Sprague-Dawley rats were anesthetized with isoflurane-oxygen, catheterized with a 24 ga. intravenous catheter (Terumo Medical) and 400 μL of 1 mg/ml protamine sulfate was instilled into the bladder. This dose of protamine sulfate is ¹⁄₁₀th that usually used and produces minimal visible urothelial damage. The protamine sulfate was removed after 10 minutes and the animals were returned to their cages. Beginning at 9 a.m. the following day (Day 1), the animals were again anesthetized with isoflurane-oxygen and were instilled with either 400 μl of 20 mg/ml SuperGAG in saline or saline alone as a control. For comparison because CS is used clinically, a set of animals were instilled with 400 μl of 20 mg/ml CS. Because the interaction with the bladder wall is likely electrostatic through the negative charges on the GAG chains, equal weights of SuperGAG and CS were compared. Beginning at 12 p.m. the rats were euthanized, and the bladder was isolated. The bladder was opened and mounted whole, urothelium side up, using a small chamber clamped over the urothelium. The electrophysiologic variables of potential difference (PD) and short circuit current (Isc) were measured to assess TEER in both bladder and colon as described previously. Sham-treated animals were instilled with saline instead of protamine sulfate or SuperGAG/CS to account for any artifacts of catheter damage.

Bladder sensitivity was assessed using von Frey filaments applied to the suprapubic region in the rat model. Female OVX rats were infused intravesically with protamine sulfate (1 mg/ml), and 24 hours later treated with i) vehicle, ii) CS (20 mg/ml) or iii) SuperGAG (20 mg/ml). Controls consisted of animals receiving a sham instillation instead of protamine sulfate or any treatment. Bladder sensitivity was assessed 3 hours later. Each von Frey filament was applied for 1-2 seconds for 10 applications. The filaments were tested from lowest to highest force. Sharp retraction of the abdomen, immediate licking or grooming or jumping was considered a positive response.

The URO-MCP-1 transgenic model was described previously. Cystitis with accompanying permeability were induced by intravesical administration of LPS at a subnoxious dose of 1 jig of LPS in 100 μl of saline (Day 0, 9 a.m.). One control group was administered saline (100 μl) only (saline URO-MCP-1). Another control group consisting of wild-type (WT) mice was also administered saline only (saline-WT). Bladders were flushed 3 times with saline to remove any excess LPS 1 hour post-LPS injection. The next day (Day 1, 9 am) animals were treated with CS or SuperGAG (20 mg/ml in saline; 100 μl) or saline and the initial permeability was assessed 3 hours later (Day 1, 12:00 p.m.).

For MRI assessment of permeability, mice were anesthetized and treated as described above, but instead of euthanizing the mice, on Day 1, Day 3, and Day 5 the mice were anesthetized, instilled with the contrast agent Gd-DTPA and placed into the MRI instrument. MRI experiments were conducted on a 7 Tesla 30 cm-bore Bruker Biospec MRI system (Bruker Biospin Corporation, Woodlands, TX, U.S.A.). MRI scans were obtained at 1-, 3-, and 5-days following LPS instillation. For the bladder images, Gd-DTPA (0.034 mM Gd-DTPA diluted to 100 μl in saline), was administered via an intravesical catheter, for visualization of loss of permeability of the bladder urothelium. Bladder CE-MRI signal intensity changes were determined 7 minutes. post-contrast. For all MR images, a T1-weighted RARE (rapid acquisition with relaxation enhancement) MRI pulse sequence was used with the following parameters: repetition time (TR) of 1200 ms, echo time (TE) of 9 ms, a RARE factor of 4, 4 averages, an image slice thickness of 1 mm, a matrix of 256×256, a field-of-view (FOV) of 3.5×3.5 cm2, and with both motion and fat suppression. Animals were euthanized and the bladders placed in formalin for histopathology.

MRI signal intensities were measured from regions-of-interest (ROIs) within images (4-5 ROIs were taken in high-intensity regions in the bladder periphery along with corresponding regions in saline control animal datasets) displayed on Paravision (v 5.0, Bruker Biospin).

SuperGAG instillates were more effective than vehicle control in restoring bladder impermeability in the protamine sulfate rat model. TEER measurements of excised bladder membrane from the protamine sulfate-rat model performed 3 hours after treatment with biopolymers. (# of rats per group in parentheses). Sham treated controls showed TEER=2500±249 Ωcm. Restoration of impermeability reduces pain response. OVX female rats were infused intravesically with 1 mg/ml protamine sulfate, and 24 hr later treated with vehicle, CS (20 mg/ml) or SuperGAG-1 (20 mg/ml). Controls consisted of animals receiving a sham instillation instead of protamine sulfate or any treatment or protamine sulfate followed by vehicle. Bladder sensitivity was assessed 3 hours later using von Frey filaments applied to the suprapubic region. Each filament was applied for 1-2 sec for 10 applications. The filaments were tested from lowest to highest force. Sharp retraction of the abdomen, immediate licking or grooming or jumping was considered a positive response. At moderate pressures (2-4 g), Super-GAG reduced the pain response by half or more and was more effective than CS in relieving pain. At higher forces (15 g), the pressure likely affected organs other than the bladder and overwhelmed any palliative effect.

SuperGAGs improved bladder permeability in the URO-MCP-1 IC mouse model as compared to control. There was a significant increase in the percent change in MM signal intensity in LPS-treated URO-MCP-1 mice, compared to saline-treated URO-MCP-1 mice (**$p<0.0001$), or the LPS-treated URO-MCP-1 mice, compared to saline-treated WT mice (**$p<0.0001$). SuperGAG restored increased bladder permeability to near-normal levels in a UROMCP-1 model for interstitial cystitis. Equal weights of CS were instilled with the SuperGAG and the CS monomers (20 mg/ml), which is also the dose used clinically. There was a significant decrease in the percent change in Mill signal intensity (SI) in SuperGAG- or CS-administered LPS-treated UROMCP-1 mice, compared to LPS-treated URO-MCP-1 mice (*$p<$for both on day 1; *$p<0.0001$ for both on day 3). Only SuperGAG LPS URO-MCP-1 mice had significantly decreased the % change in Mill SI on day 5, compared to LPS URO-MCP-1 mice ($p<0.01$).

The data demonstrates that with the URO-MCP1 transgenic mouse model, and using CE-MRI to assess permeability, SuperGAG restores the bladder permeability to normal values. Sub-noxious dose of LPS induces bladder permeability whereas instillation of saline does not, for either saline-treated URO-MCP1 or wild type mice. Representative images of bladders, control, saline-treated URO-MCP1, protamine sulfate-treated and saline treated wild type mice. Note that in the rat protamine sulfate model normal control values are high (2500 Ωcm2) whereas in the mouse LPS model permeability is assessed directly with CE-MM, and normal values are low. In the case of the mouse model, the control refers to values obtained with treatment to induce permeability, and then vehicle is administered instead of an agent to restore impermeability. The change over time determined by repeat determinations on days 1, 3, and 5 with the same mice treated either with LPS only (Control-PPS), SuperGAG (S-GAG) or CS. The small effect size in comparing the SuperGAG prep and CS would require a much larger sample size to test for statistical significance. Nonetheless, the data indicate that SuperGAG is more effective than CS, particularly at day 5 following treatment, as it was significantly lower than the control, whereas CS was not significantly different to control.

EQUIVALENTS

It is to be understood that while the disclosure has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

What is claimed is:

1. A method of preparing a water-soluble sulfated GAG conjugate, comprising the steps of:
    i) contacting a sulfated GAG in aqueous solution at a concentration of 2 wt %-20 wt % with an effective amount of linking agent, wherein the molar ratio of GAG hydroxyl groups to linking agent is less than that required for gel formation, under conditions sufficient to react the linking agent with the sulfated GAG to form a solution comprising a soluble polymer characterized by pendant linking groups;
    ii) adding additional sulfated GAG to the solution of step (i) in an amount sufficient to react with a portion of the pendant linking groups to form a soluble polymer conjugate with a branched architecture characterized by remaining pendant linking groups; and
    iii) adding a modifier characterized by a reactive moiety under conditions sufficient to react the remaining pendant linking groups with the reactive modifier to form a water-soluble sulfated GAG branched conjugate bearing the modifier.

2. The method of claim 1, wherein the product of step i) has a substantially linear structure.

3. The method of claim 1, wherein the sulfated GAG conjugate product of step-iii has a molecular weight of 100,000 Da to 5,000,000 Da.

4. The method of claim 1, wherein the sulfated GAG of step-i has a molecular weight of about 1,000 Da, 5,000 Da, 10,000 Da, 15,000 Da, 20,000 Da, 30,000 Da, 40,000 Da, 50,000 Da, 100,000 Da, or a range including any two of these numbers, preferably between 5,000 Da and 30,000 Da.

5. The method of claim 1, wherein the ratio of GAG hydroxyl group equivalents, present in the solution of step i), to moles of linking agent is 0.8 to 4.0.

6. The method of claim 1, wherein the sulfated GAG of step i) is identical to that added in step ii).

7. The method of claim 1, wherein the pendant reactive group is vinyl.

8. The method of claim 1, wherein the linking agent is divinyl sulfone.

9. The method of claim 1, wherein pendant reactive groups are present in the soluble polymer formed in step ii) on between 2% and 30% of disaccharide repeat units, as determined by proton NMR.

10. The method of claim 1, wherein the total amount of sulfated GAG added in steps i and ii is apportioned in a ratio between 15/85 and 80/20.

11. The method of claim 1, wherein the reactive moiety of the modifier introduced in step-iii is an amine.

12. The method of claim 1, wherein the modifier comprises a targeting moiety.

13. The method of claim 1, wherein the modifier is lactosylamine.

14. The method of claim 1, wherein the modifier comprises a hydrophobic moiety.

15. The method of claim 1, wherein the water-soluble GAG conjugate comprises one or more residual unreacted linker groups capable of forming covalent bonds with mammalian tissue in situ.

* * * * *